United States Patent [19]

Igari et al.

[11] Patent Number: 5,591,713
[45] Date of Patent: Jan. 7, 1997

[54] WATER-SOLUBLE COMPOSITION FOR SUSTAINED-RELEASE

[75] Inventors: Yasutaka Igari, Kobe; Minoru Yamada, Kawanishi; Yasuaki Ogawa, Kyoto, all of Japan

[73] Assignee: Takeda Chemical Industries, Ltd., Osaka, Japan

[21] Appl. No.: 377,392

[22] Filed: Jan. 24, 1995

Related U.S. Application Data

[60] Division of Ser. No. 909,160, Jul. 6, 1992, Pat. No. 5,416,071, which is a continuation-in-part of Ser. No. 847,188, Mar. 6, 1992, abandoned.

[30] Foreign Application Priority Data

Mar. 12, 1991 [JP] Japan .................. 3-046735
Jul. 10, 1991 [JP] Japan .................. 3-170205

[51] Int. Cl.$^6$ .................................................. A61K 37/10
[52] U.S. Cl. ................................. 514/8; 514/4; 514/12; 514/21
[58] Field of Search ........................ 514/4, 8, 12, 21

[56] References Cited

U.S. PATENT DOCUMENTS

| | | | |
|---|---|---|---|
| 3,959,247 | 5/1976 | Fujino et al. | 260/112.5 |
| 4,100,152 | 7/1978 | Fujino et al. | 260/112.5 |
| 4,879,111 | 11/1989 | Chong | 424/85.1 |
| 5,416,071 | 5/1995 | Igari | 514/8 |

FOREIGN PATENT DOCUMENTS

| | | | |
|---|---|---|---|
| 0045222 | 2/1982 | European Pat. Off. | C12N 9/02 |
| 0070656 | 1/1983 | European Pat. Off. | C12N 11/00 |
| 0145390 | 6/1985 | European Pat. Off. | C07K 13/00 |
| 0176299 | 4/1986 | European Pat. Off. | C07K 3/16 |
| 0224987 | 8/1986 | European Pat. Off. | |
| 2606309 | 8/1976 | Germany . | |
| 3-63299 | 3/1991 | Japan . | |
| WO90/05522 | 5/1990 | WIPO | A61K 9/22 |
| WO90/09798 | 9/1990 | WIPO | A61K 37/00 |
| WO91/00739 | 1/1991 | WIPO | A61K 37/24 |
| WO91/04058 | 4/1991 | WIPO | A61K 47/36 |

OTHER PUBLICATIONS

Abstract # 90–047916 (Jan. 5, 1990).
Abstract # 90–004036 (Nov. 1989).
Derwent Abstract No. 91–122603/17 corresponding to JP 3-63299-A (Laid–Open).
Derwent Abstract No. 90–004036/01 corresponding to JP 1-287041/1989 (Laid Open).
Derwent Abstract No. 90–047916/07 corresponding to JP 2-213/1990 (Laid Open).
Derwent Abstract No. 91–054446/08 corresponding to JP 3-4790/1991 (Laid Open).
Endocrinology, vol. 129, No. 1, pp. 323–329 (Jul.–Dec. 1991).
The EMBO Journal, vol. 11, No. 5, pp. 1867–1873 (1992).
The Journal of Biological Chemistry, vol. 252, No. 15, pp. 5558–5564 (1977).
The Journal of Biological Chemistry, vol. 262, No. 35, pp. 17156–17163 (Dec., 15, 1987).
Nature, Vil. 313, No. 28, pp. 806–810 (Feb. 1985).
Proc. Natl. Acad. Sci., vol. 82, pp. 7580–7584 (Nov. 1985).
Proceedings of the National Academy of Sciences, vol. 86, pp. 7819–7822 (Oct. 1989).
Endocrinology, vol. 116, No. 6, pp. 2293–2299 (Jan.–Jun. 1985).
Biochimica et Biophysica Acta, vol. 1038, pp. 125–129 (1990).
Agricultural and Biological Chemistry, vol. 52, (6), pp. 1575–1581 (1988).

*Primary Examiner*—Edward J. Cain
*Attorney, Agent, or Firm*—David G. Conlin; George W. Neuner; Cara Z. Lowen

[57] ABSTRACT

(1) A composition which comprises erythropoietin and hyaluronic acid shows a sustained-release of the medicine in a living body, and
(2) A water-soluble composition which comprises (a) a pharmacologically active polypeptide secreted by an animal body or its derivative or a chemically synthesized pharmacologically active substance, (b) a water-soluble species' of hyaluronic acid or its nontoxic salt and (c) a water-soluble protein injectable into body fluids without showing any substantial pharmacological activity brings about a prolonged action in vivo of a pharmacologically active substance. In addition, the composition can be administered using a small-gauge needle and thereby contributes to relieving pain in patients.

14 Claims, 15 Drawing Sheets

WATER-SOLUBLE COMPOSITION FOR SUSTAINED-RELEASE

This is a divisional of application Ser. No. 07/909,160 filed on Jul. 6, 1992 U.S. Pat. No. 5,416,071, which is a Continuation in Part of Ser. No. 07/847,188 filed on Mar. 6, 1992 abandoned.

FIELD OF THE INVENTION

The present invention relates to a water-soluble composition which is of value as a sustained-release preparation of a pharmacologically active substance.

BACKGROUND OF THE INVENTION

Erythropoietin is known to act on erythroblastic progenitor cells in bone marrow to promote their differentiation into red blood cells. However, this substance has been made available only by the process of extracting and purifying it from human urine, thus preventing its clinical application on a large scale. With rapid progresses in recombinant DNA technology in recent years, it became possible to mass-produce erythropoietin analogs which are similar to the natural erythropoietin of human origin. These substances contributed dramatically to the improvement of renal anemic symptoms in patients with those diseases which are suspected to be chiefly associated with compromised erythropoietin production, and a further expansion of the clinical utility of erythropoietin is foreseen.

Today, erythropoietin is clinically administered to patients by the intravenous route but since the excretion of this substance after administration is fairly rapid, it must be administered as often as twice to three times a week. Moreover, the elevation of hemoglobin concentration and of hematocrit level is preferably gradual and any abrupt rises in these parameters would increase adverse reactions such as hypertension. Thus, side effect is a serious concern if a high blood concentration is reached immediately after administration, as is inevitable in the case of intravenous injection. Therefore, some proposals have been made for overcoming this disadvantage accompanying the administration of physiologically active peptides.

Long-acting preparations of a medicine are generally designed to maintain a sustained blood level of the medicine in humoral fluid but according to the mechanism of development of pharmacologic effects involved, medicine of this kind may generally be classified into two categories. The first category (a) is such that the pharmacologic effect of the medicine is not very dependent on effective humoral concentration and an excess of pharmacologic effect is not so detrimental to the recipient's physiology. The second category (b) is such that the pharmacologic effect of the medicine is dependent on effective humoral concentration and because the abrupt onset of its pharmacologic effect or an excessive pharmacologic effect is harmful to the body, the dosage must be adjusted from time to time.

Because of its dramatic pharmacologic effect, erythropoietin requires a caution in its use so that hypertension due to more than necessary hematopoiesis should be prevented. In this sense, erythropoietin is a peptide drug belonging to category (b), which calls for frequent (for example, once in about a week) efficacy evaluation and dosage adjustment.

Meanwhile, since the activity of erythropoietin is dependent on its three-dimensional structure, it is essential, in the pharmaceutical manufacturing stage, to avoid formulations which might affect the spatial configuration of the peptide.

Therefore, should a long-acting preparation be developed that would insure a sustained efficacy of erythropoietin for a period of time corresponding to an interval of efficacy assessment (for example once in about a week), the current administration frequency of 3 times a week would be reduced to benefit the patient a great deal. This benefit not only should accrue to patients with renal anemia but also would be remarkable for patients in the field of surgery involving autologous blood transfusions where both the administration frequency and the dosage level could be decreased with great rewards. Moreover, it should be possible to minimize the abrupt increase in drug concentration immediately following administration and thereby suppress the excess reactions due to a precipitating onset of the pharmacologic action.

On the other hand, hyaluronic acid is a naturally-occurring acid mucopolysaccharide and has been used as an ethical drug such as an articular function-improving agent or an adjunct in ophthalmic surgery. It is known that an aqueous solution of hyaluronic acid has a high viscosity which generally retards diffusion of other substances.

In Japanese Patent Application Laid-open No. 62-129226 (1987) which corresponds to European Patent Publication No. 224,987, it is disclosed that a solution of hyaluronan including hyaluronic acid, its sodium salt, or hylan can release dissolved or dispersed pharmacologically active substances sustainedly due mainly to the viscosity of the solution of hyaluronan. In addition, those pharmacologically active substances that have cationic residues are diffused more slowly owing to an ionic exchange between the cationic residues and the carboxylic acid of hyaluronan. In the description of one of the working examples, tritium-labeled serotonin mixed with 0.1% aqueous solution of hyaluronic acid was put into an semi-permeable dialysis membrane bag (molecular weight cut off=10,000) and dialyzed against distilled water. The release rate of the tritium-labeled serotonin from the dialysis bag was reduced some ten-fold compared with the comparative example where no hyaluronic acid was employed.

By utilizing the above mentioned property, Japanese Patent Application Laid-open No. 1-287041 (1989) teaches a controlled release system containing hyaluronic acid or its pharmaceutically acceptable salt and, as particularly suitable physiologically active peptides, mentions insulin, crystalline insulin zinc, amorphous insulin zinc and glucagon. In the description of working examples, the above patent literature mentions as follows. When hyaluronic acid (molecular weight 1,400,000, viscosity method) was added to a neutralized injectable solution of swine insulin at a final concentration of 1% and the resulting composition was administered subcutaneously to normal male rabbits, an overt prolongation of hypoglycemia was found as compared with a positive control group of rabbits treated with insulin alone. Thus, this depressed blood glucose level was sustained at least till 12 hours following administration and, then, this effect had disappeared by 24 hours. The same literature contains a similar example for glucagon as well and mentions that the blood glucose resumed at latest by 8 hours after administration.

Japanese Patent Application Laid-open No. 2-213 (1990) also discloses a sustained release system for biologically active peptides which incorporates hyaluronic acid or its nontoxic salt. When, in working examples, a sustained release preparation of calcitonin or elcatonin containing 5% sodium hyaluronate was administered subcutaneouly to male rats, the depression of blood calcium persisted for a minimum of 12 hours. Similarly, when a sustained release system for human growth hormone containing 5% of sodium hyaluronate was administered to male rats, the blood human growth hormone level was sustained for at least 12 hours. In either case, prolongation of blood concentration was evident as compared with the corresponding comparative example in which sodium hyaluronate was not employed.

However, none of the above inventions allude to erythropoietin, whether by way of general description or as a working example.

These published inventions invariably utilize the phenomenon of delayed diffusion of ingredients in solutions of hyaluronic acid at the administration site, and Japanese Patent Application Laid-open No. 2-213 (1990) mentions that the most preferred concentration of hyaluronic acid itself is 3 to 7%. However, because of the high viscosity of the hyaluronic acid solution, removal of the air foam represents a serious technical challenge, calling for evacuation by centrifuging or decompression. Furthermore, also because of the high viscosity, it is necessary to employ a large-gauge needle for injection which gives the patient a pain which cannot be disregarded. Japanese Patent Application Laid-open No. 1-287041 (1989) is reticent about the concentration of hyaluronic acid used but contains working examples employing 1% hyaluronic acid. However, the precautions of the package insert for Artz (Kaken Pharmaceutical), which is a 1% sodium hyaluronate preparation for articular injection, recommend the use of a comparatively large-gauge needle of about 18 to 20 G. Therefore, the pain which these preparations for subcutaneous injection give to the patient is considerable.

Furthermore, Japanese Patent Application Laid-Open No. 3-4790 (1991) discloses an aqueous system that comprises polysaccharides, proteinases, and protein-like substances. It is disclosed that the system stabilizes the proteinases and prevent the loss of enzyme activity during storage especially at high temperature. In working examples, the combination of hyaluronic acid and either bovine serum albumin or gelatin prevented the loss of activity of esperase(Novo) produced by *Becillus licheniformis* better than the corresponding comparative examples in which either hyaluronic acid alone or protein alone was employed. However, this technique never alludes to sustained release of ethical drugs, especially erythropoietin, from the system when administered to living bodies.

Accordingly, there is a desire in the art to provide a long-acting medicine composition containing erythropoietin or other pharmacologically active substance which insures sufficient efficacy at a dosing interval of, for example, about one week through prolongation of drug release and which is lenient on the patient in terms of the pain associated with administration.

SUMMARY OF THE INVENTION

The intensive research of the present inventors for solving the above-mentioned problems revealed that when erythropoietin is mixed with hyaluronic acid, a high molecular weight compound which is known to be biodegradable and pharmacologically injectable, with the concentration of hyaluronic acid being controlled below the usual concentration, and the resulting pharmaceutical composition is administered by injection, the pharmacological efficacy of erythropoietin is sustained over a long time period without interfering with the pharmacological activity of the drug substance and, at the same time, the abrupt onset of the pharmacological effect of the drug in an early stage after administration is successfully controlled. It was also found that the above pharmaceutical composition can be easily administered using a small-gauge needle of, for example, 26 G which does not cause an appreciable pain to the patient.

The present invention provides (1) a composition for sustained release of erythropoietin, which comprises erythropoietin, hyaluronic acid or its nontoxic salt and a pharmaceutically acceptable carrier, diluent or excipient, and (2) a method for producing a composition for sustained release of erythropoietin, which comprises mixing erythropoietin with hyaluronic acid or its nontoxic salt and a pharmaceutically acceptable carrier, diluent or excipient.

Furthermore, the present inventors made intensive investigations in an attempt to solve the above problems and, as a result, found that water-soluble compositions containing a pharmacologically active substance, a water-soluble species of hyaluronic acid and a water-soluble protein injectable into body fluids without showing any substantial pharmacological activity provide, when administered, a prolonged pharmacological effect without loss in the pharmacological activity of the active substance and with suppression of abrupt manifestation of the pharmacological effect at the initial stage following administration. Based on this finding, they made continued investigations and have now completed the present invention.

Thus the invention provides a water-soluble composition which comprises (a) a pharmacologically active polypeptide secreted by an animal body or its derivative or a chemically synthesized pharmacologically active substance, (b) a water-soluble species of hyaluronic acid or its nontoxic salt and (c) a water-soluble protein injectable into body fluids without showing any substantial pharmacological activity.

In the present invention, a pharmacologically active polypeptide secreted by an animal body or its derivative or a chemically synthesized pharmacologically active substance is abbreviated as pharmacologically active substance for short.

In these representations, each graph represents the mean results for 4 rats at the minimum. Each plot represents the mean result of each group and the bar represents the standard error (S.E.).

Figure 3:
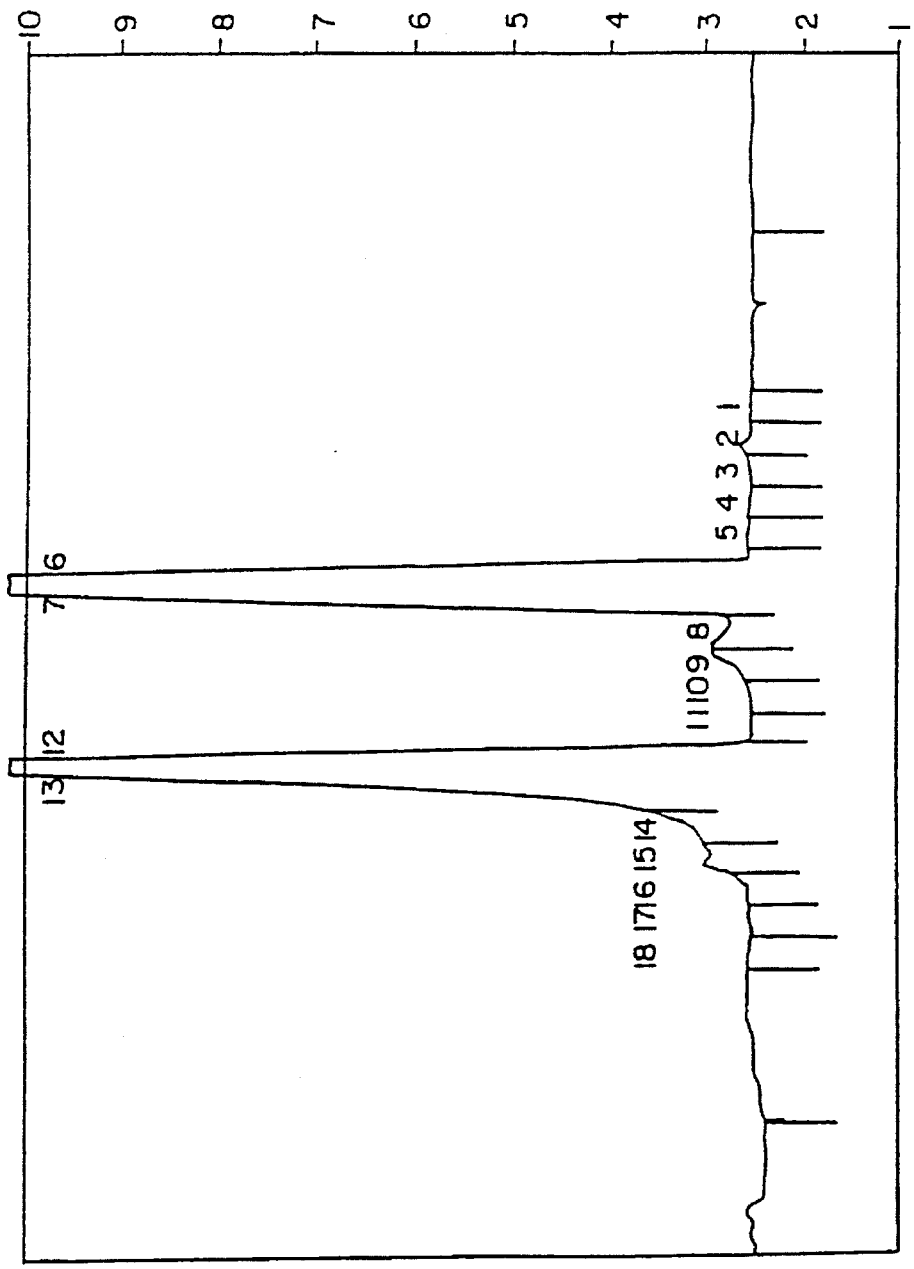

FIG. 3 is a diagrammatic representation of the chromatogram (Example 2) obtained by weak anion exchange chromatography indicating the separation of human serum albumin and epoetin beta.

Figure 4:
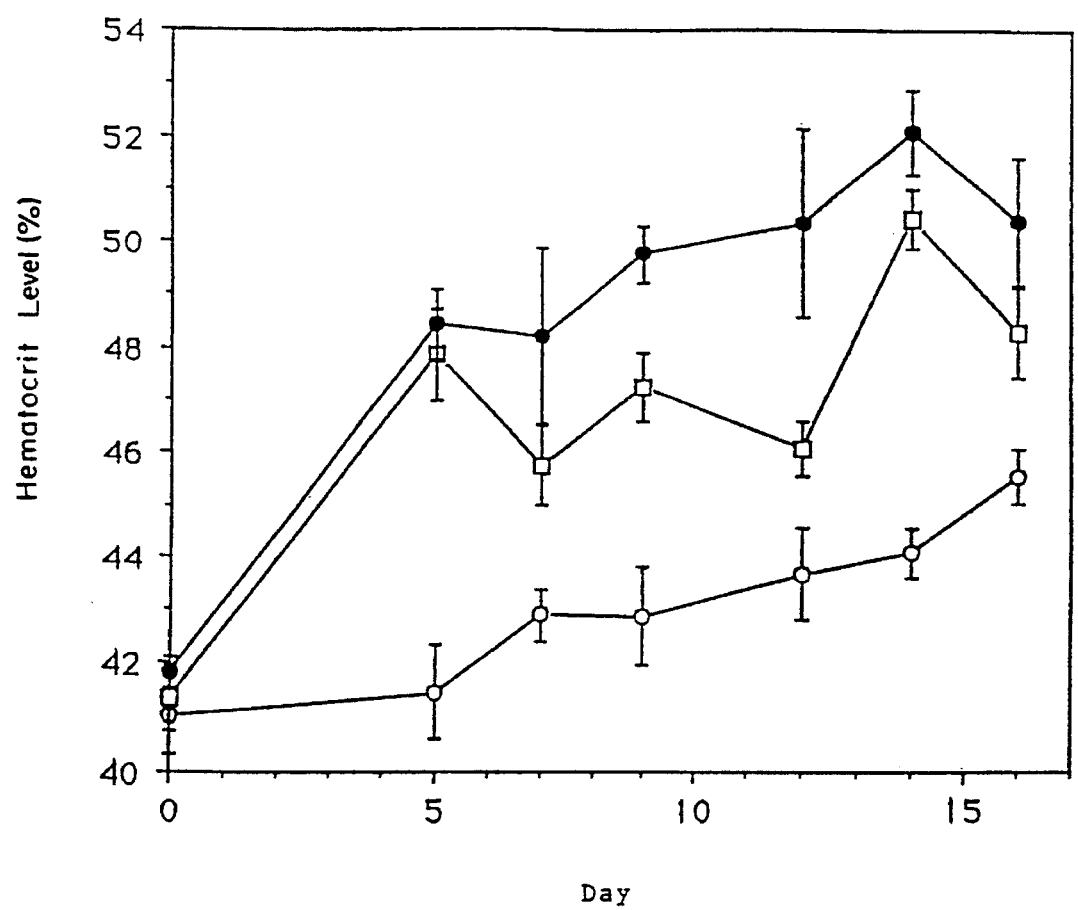

FIG. 4 is a diagrammatic representation, obtained in Experimental Example 2, of the time course (solid circles) of hematocrit level which prevailed when the erythropoietin injection (Example 2) was administered twice at an interval of one week and the time course (open squares) of hematocrit level which prevailed when the erythropoietin injection (Comparative Composition 3) was administered twice at an interval of one week. The time course (open circles) of hematocrit level which prevailed when physiological saline for injection (Comparative Composition 4) was administered is shown as well.

Figure 5:
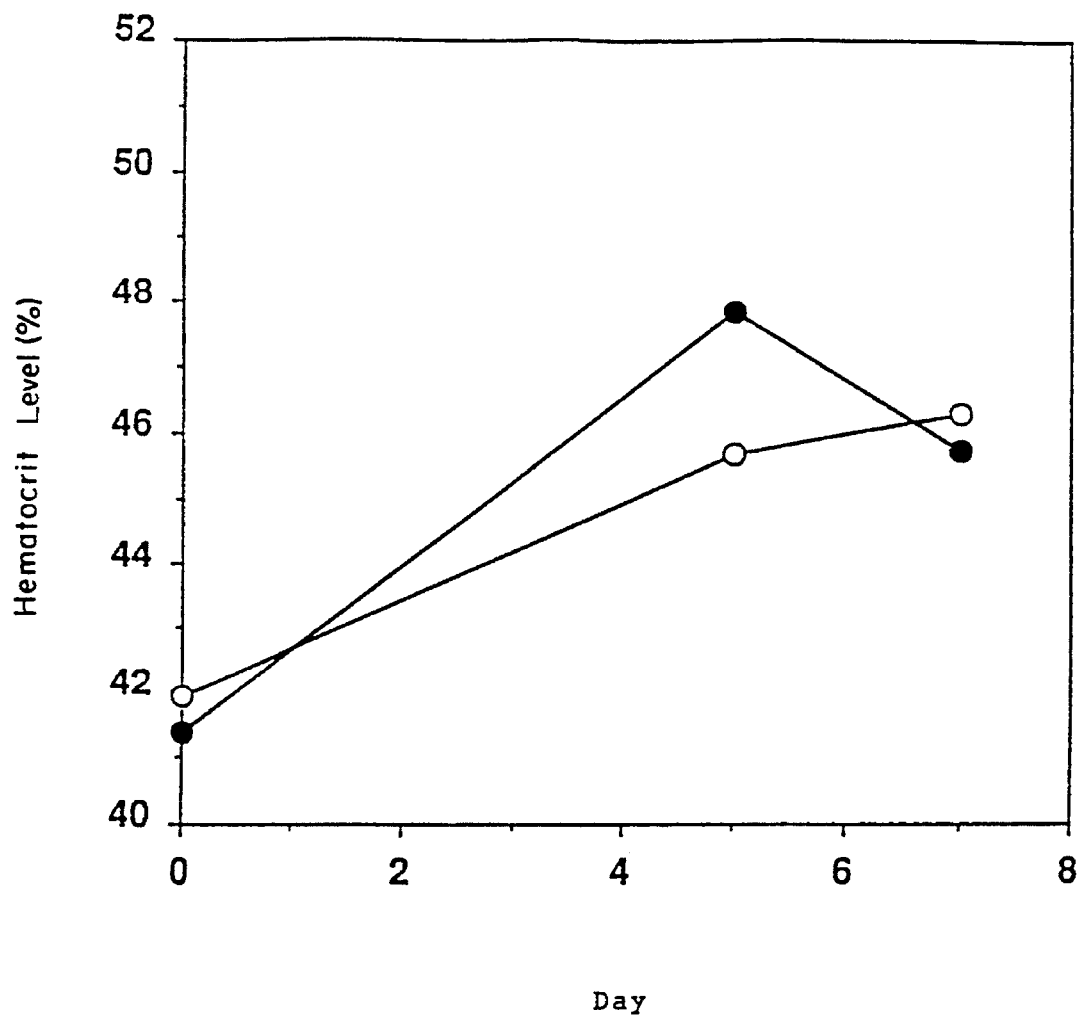

FIG. 5 is a diagrammatic representation, obtained in Experimental Example 3, of the time course (open circles) of hematocrit level which prevailed when the erythropoietin injection (Comparative Composition 5) was administered and the time course (solid circles) of hematocrit level which prevailed when the erythropoietin injection (Example 3) was administered.

Figure 6:
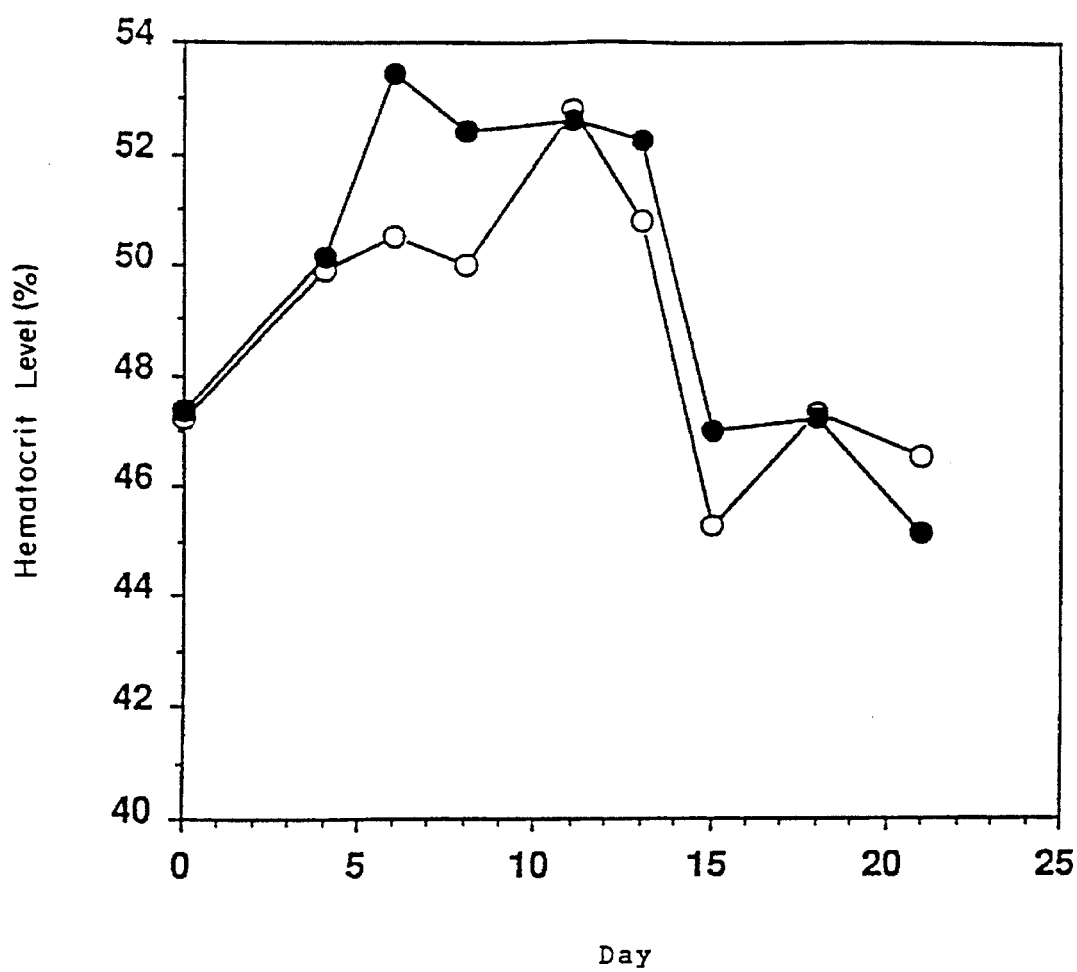

FIG. 6 is a diagrammatic representation, obtained in Experimental Example 4, of the time course (open circles) of hematocrit level which prevailed when the erythropoietin injection (Comparative Composition 7) was administered and the time course (solid circles) of hematocrit level which prevailed when the erythropoietin injection (Example 5) was administered twice one week apart, respectively.

Figure 7:
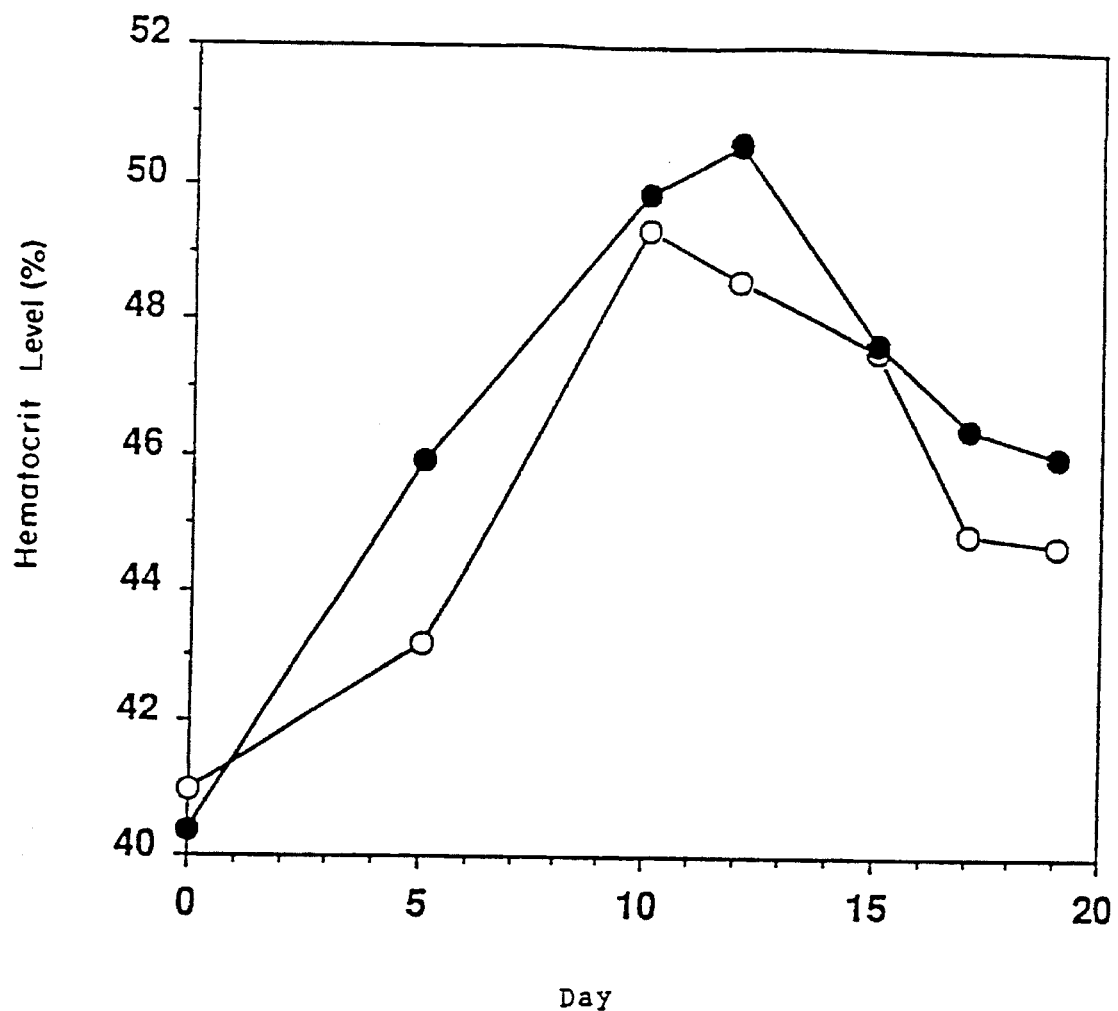

FIG. 7 is a diagrammatic representation, obtained in Experimental Example 5, of the time course (open circles) of hematocrit level which prevailed when the erythropoietin injection (Comparative Composition 9) was administered and the time course (solid circles) of the hematocrit level which prevailed when the erythropoietin injection (Example 5) was administered twice one week apart, respectively.

Figure 8:
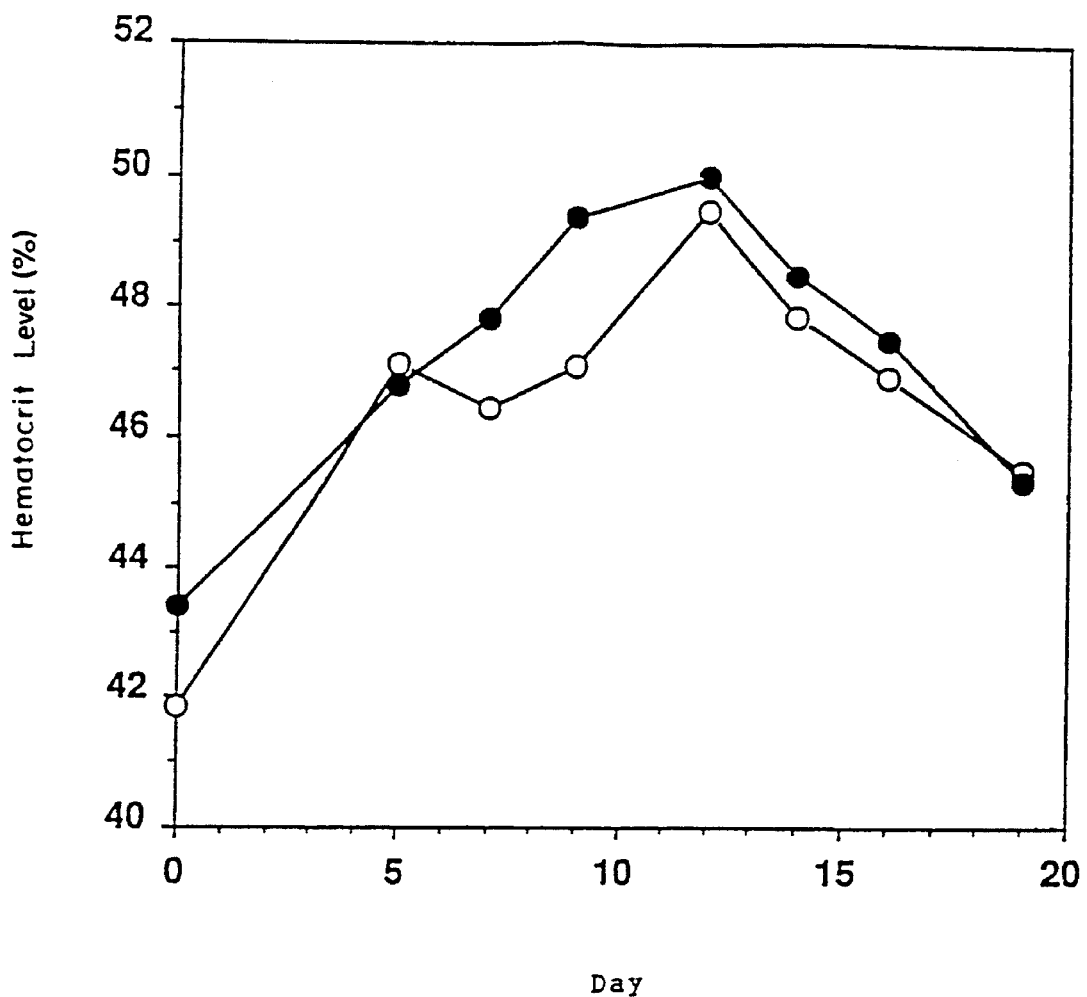

FIG. 8 is a diagrammatic representation, obtained in Experimental Example 6, of the time course (open circles) of hematocrit level which prevailed when the erythropoietin injection (Comparative Composition 11) was administered and the time course (solid circles) of hematocrit level which prevailed when the erythropoietin injection (Example 6) was administered twice one week apart, respectively.

Figure 9:
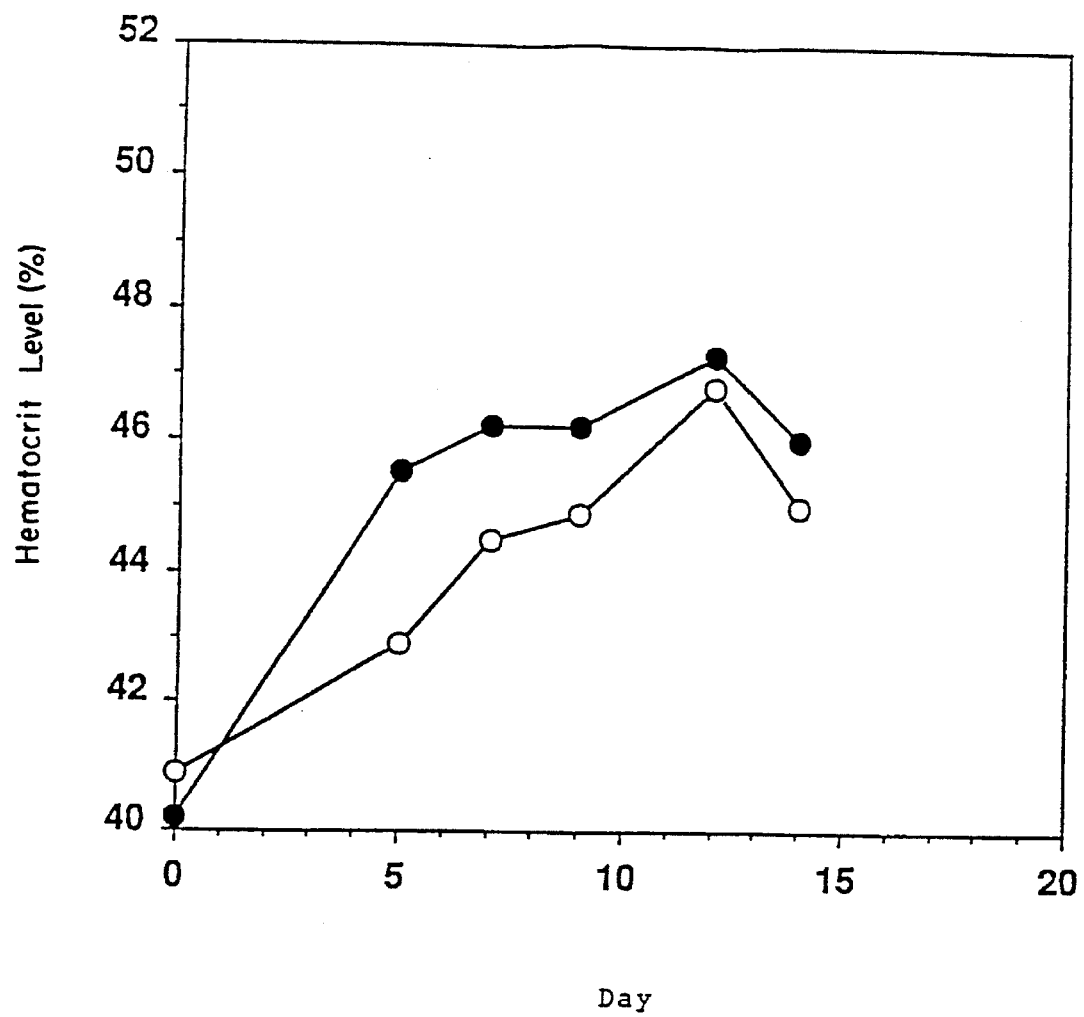

FIG. 9 is a diagrammatic representation, obtained in Experimental Example 7, of the time course (open circles) of hematocrit level which prevailed when the erythropoietin injection (Comparative Composition 13) was administered and the time course (solid circles) of hematocrit level which prevailed when the erythropoietin injection (Example 7) was administered twice one week apart, respectively.

Figure 10:
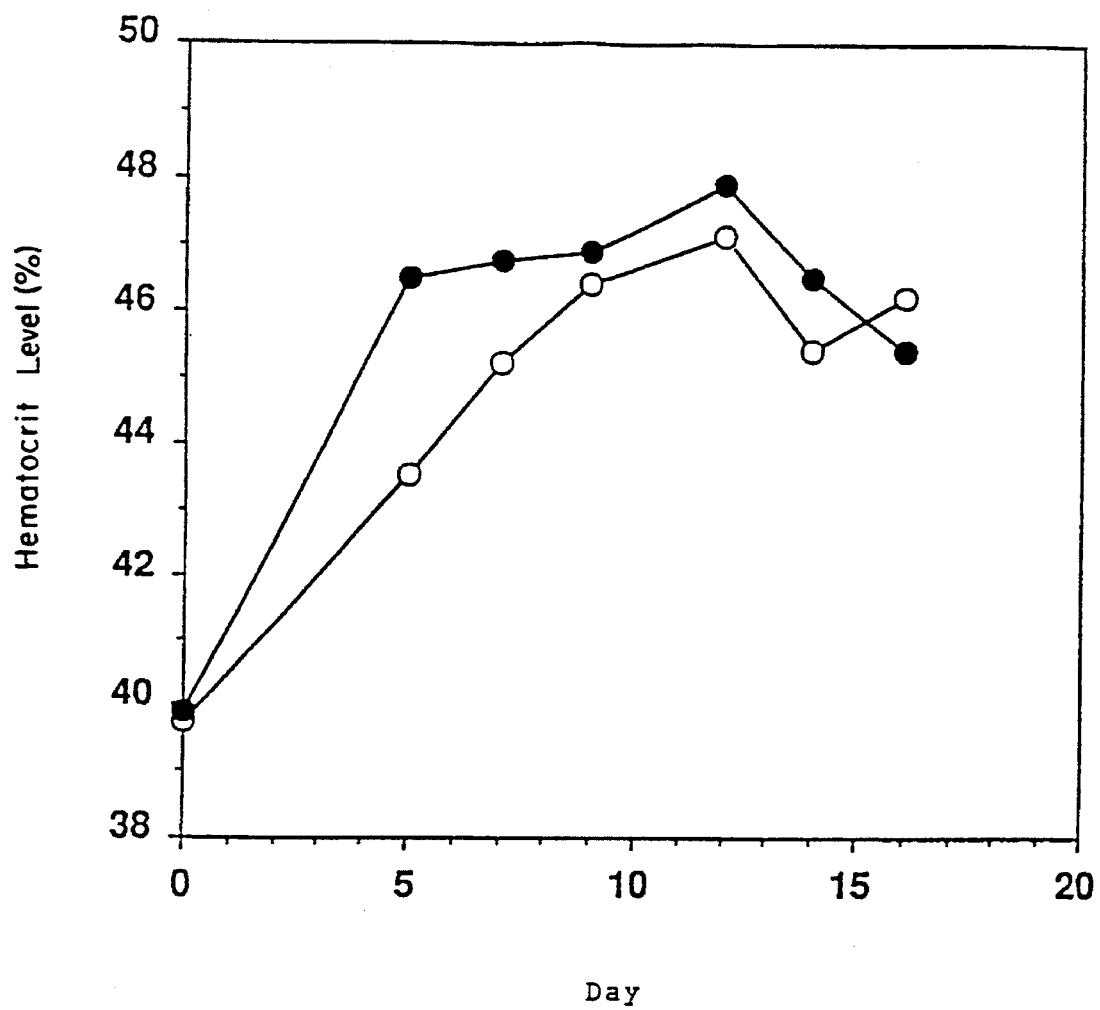

FIG. 10 is a diagrammatic representation, obtained in Experimental Example 8, of the time course (open circles) of hematocrit level which prevailed when the erythropoietin injection (Comparative Composition 15) was administered and the time course (solid circles) of hematocrit level which prevailed when the erythropoietin (Example 9) was administered twice one week apart, respectively.

Figure 11:
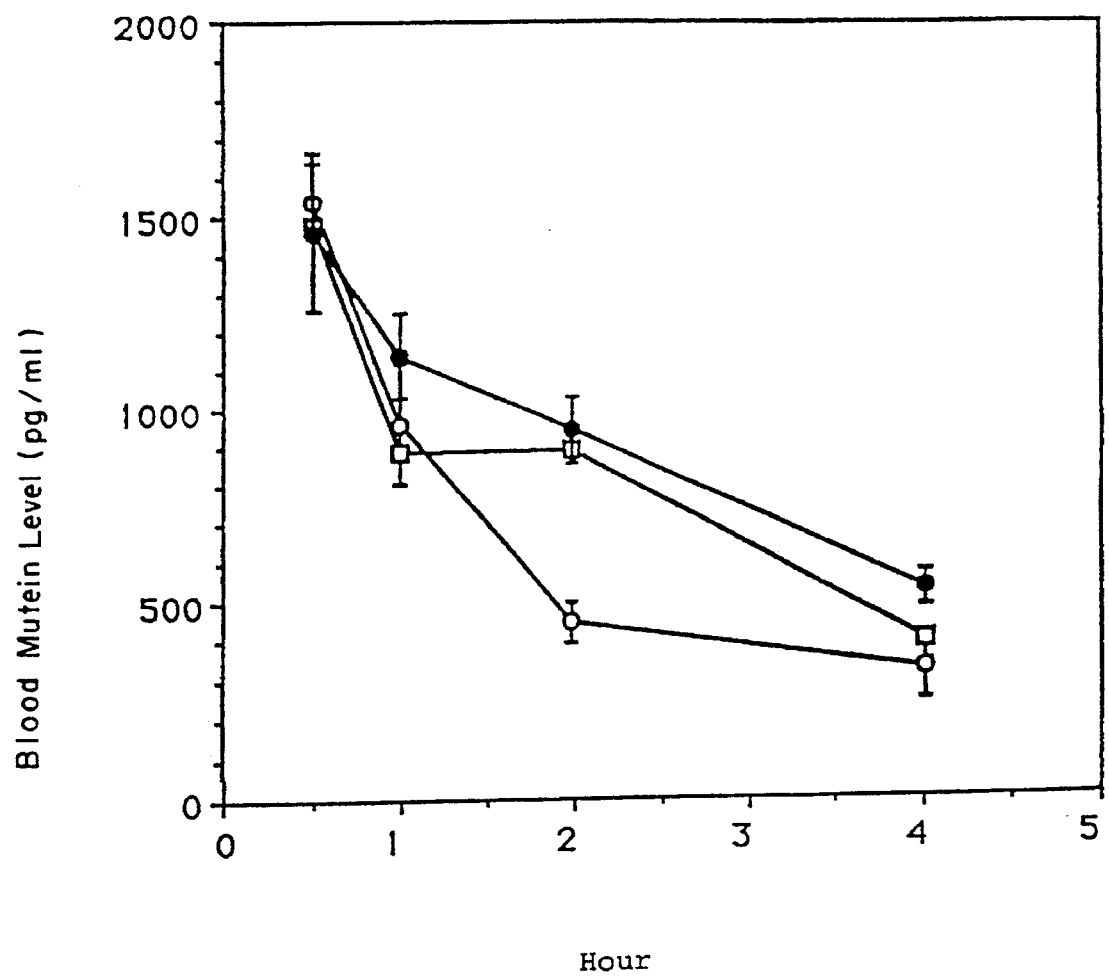

FIG. 11 shows the serum mutein drug levels, as found in Experimental Example 11.

Figure 12:
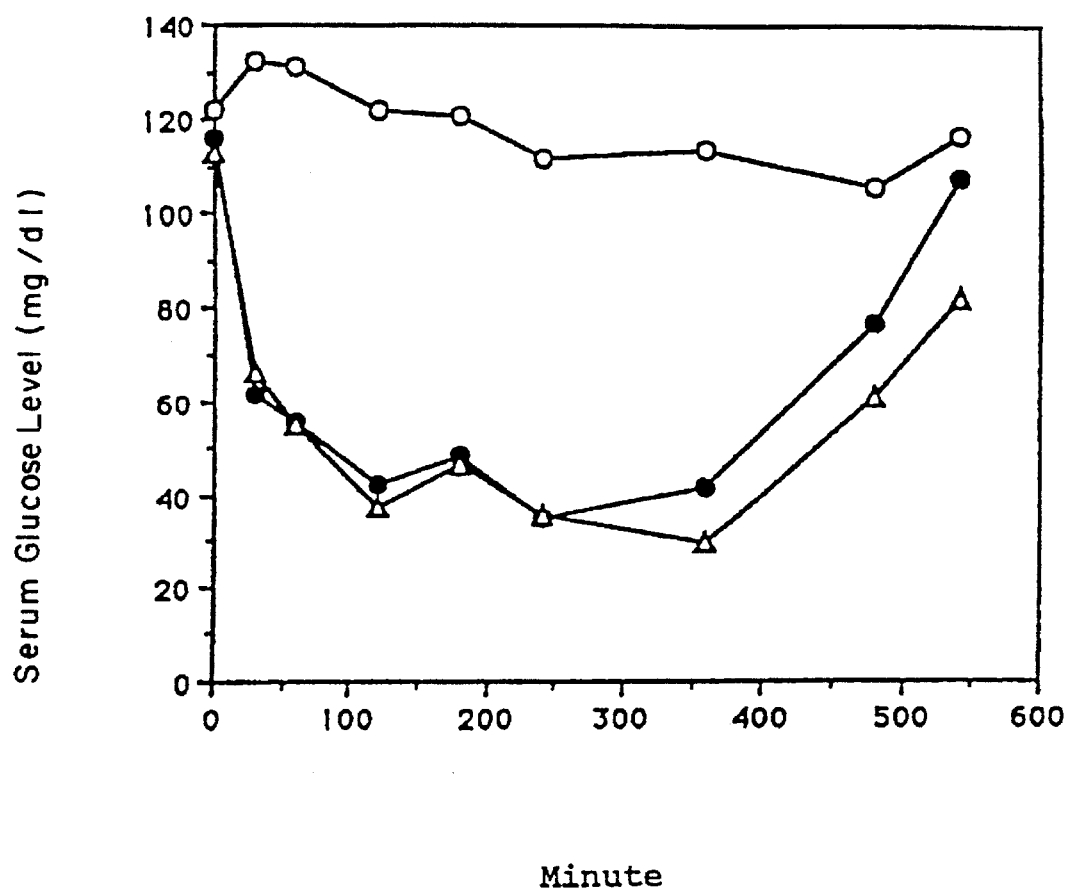

FIG. 12 shows the serum glucose levels, as found in Experimental Example 12.

Figure 13:
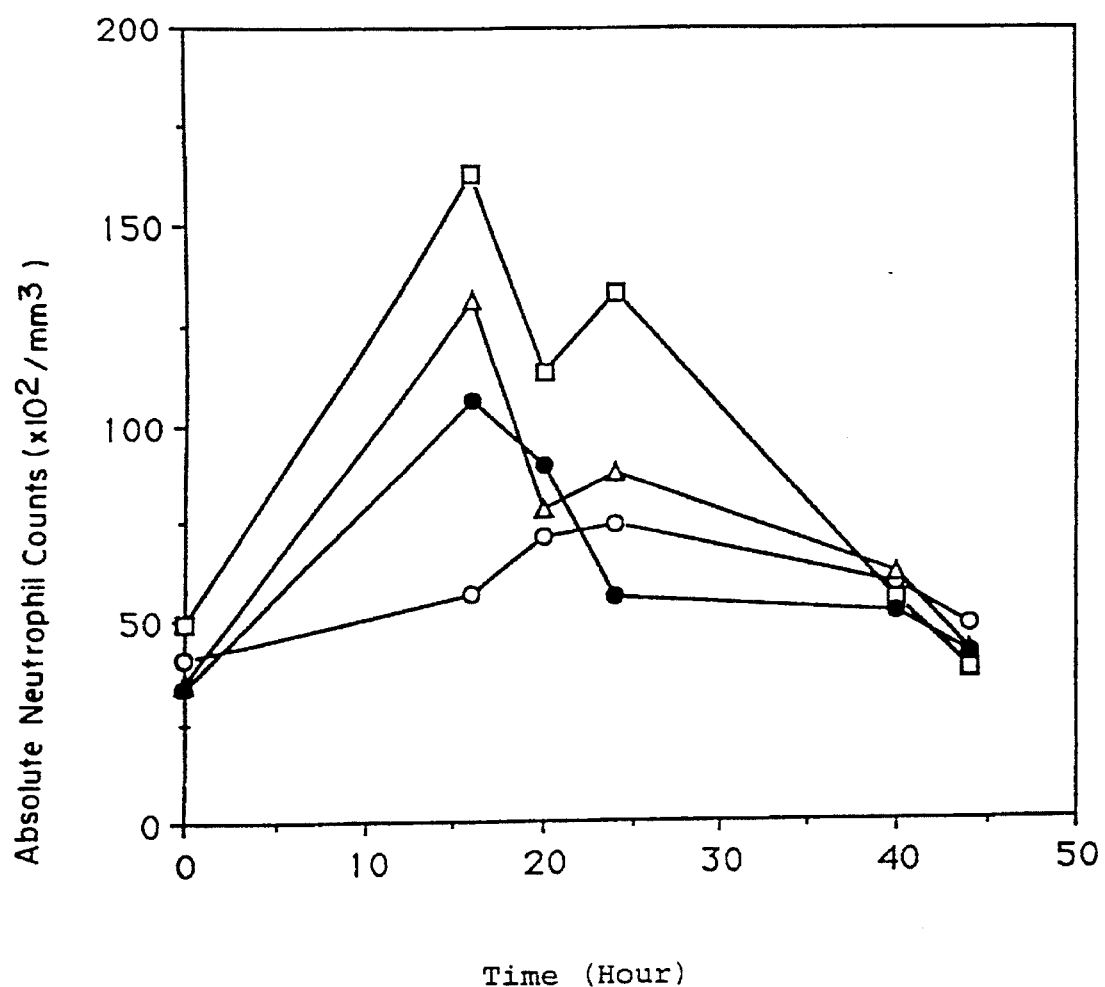

FIG. 13 shows the time course of absolute neutrophil counts in peripheral blood, as found in Experimental Example 13.

Figure 14:
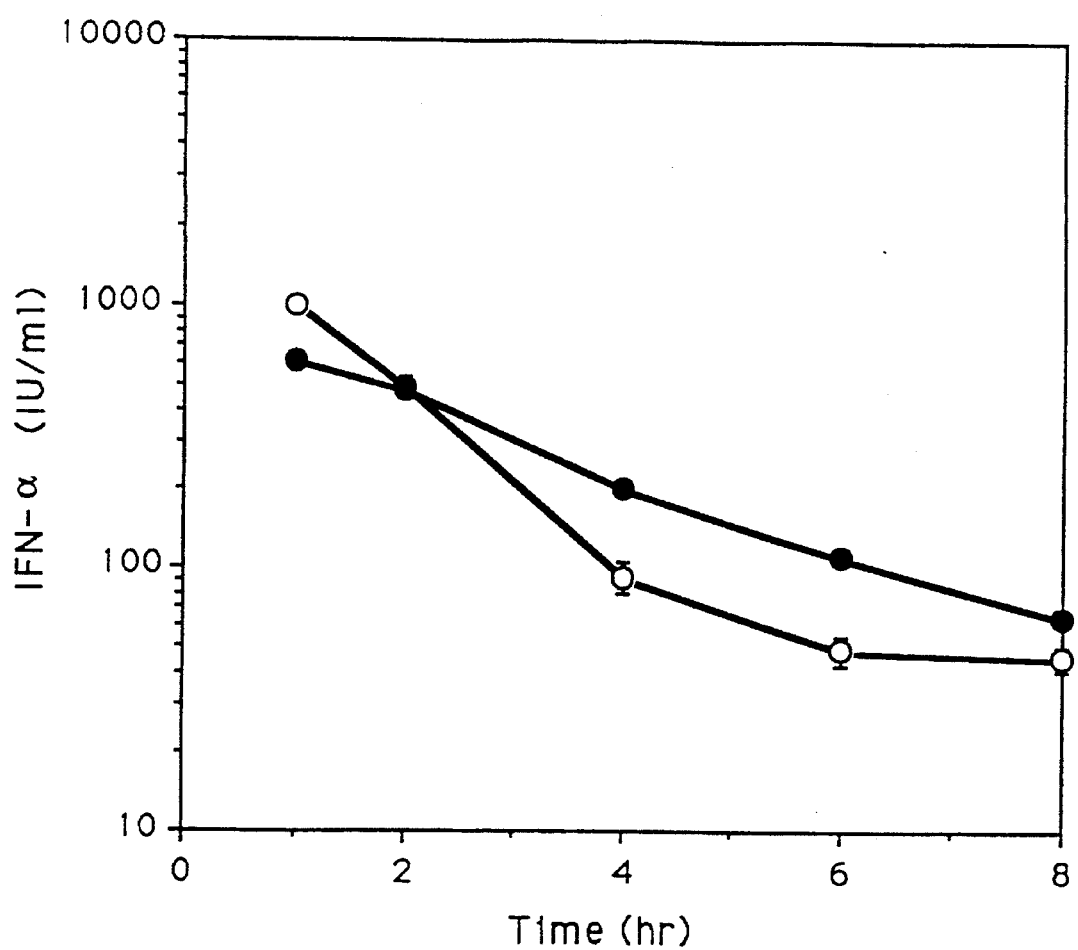

FIG. 14 shows the serum drug levels, as found in Experimental Example 14.

Figure 15:
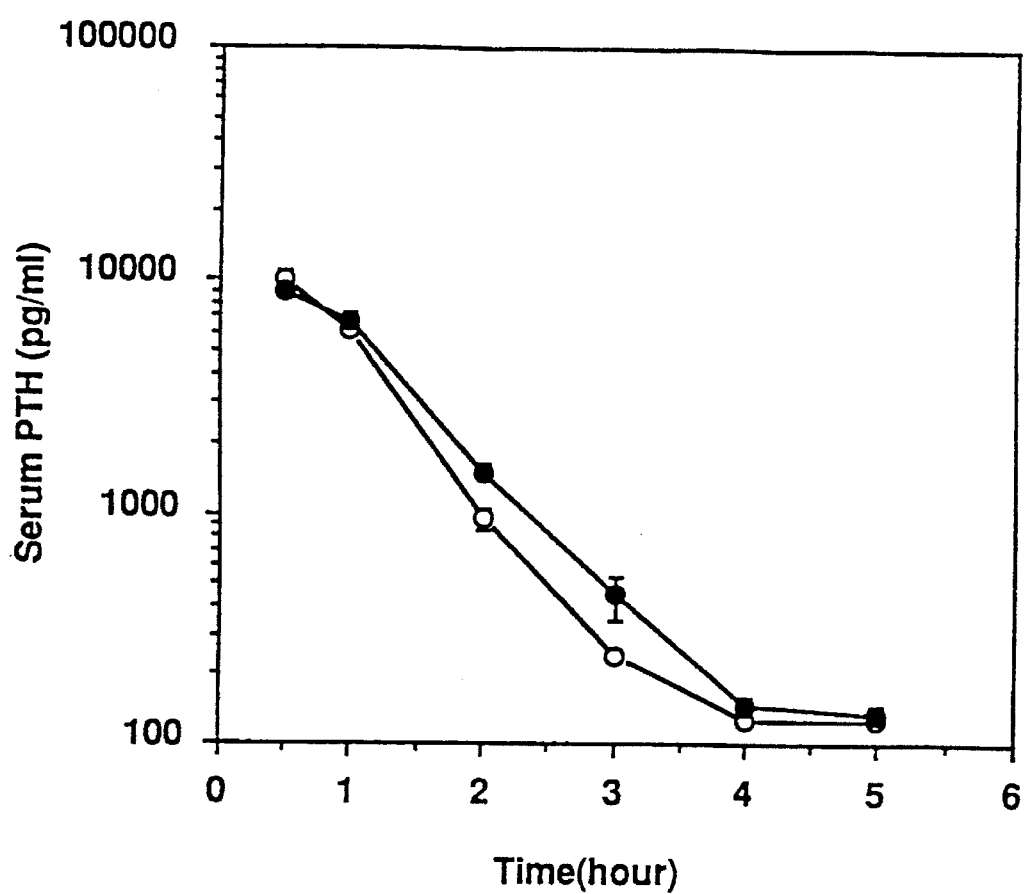

FIG. 15 shows the serum PTH levels, as observed in Experimental Example 16.

DETAILED DESCRIPTION OF THE INVENTION

In the context of the present invention, erythropoietin means a naturally occurring or recombinant erythropoietin as a hematopoietic glycoprotein, an erythropoietin differing in sugar chain but having hematopoietic activity, an erythropoietin lacking in sugar chain, a mutein different from them in partial amino acid sequence, or a derivative of any of them which has the same activity as erythropoietin, or an active fragment of any of said substances.

Examples of a naturally occuring erythropoietin include those reported by Miyake et al. (J. Biol. Chem., 252, 5558–5564 (1977)) and Recny et al. (J. Biol. Chem., 262, 17156–17161 (1987)). Examples of a recombinant erythropoietin include those reported by Jacobs et al. (Nature, 313, 806–810 (1985)), Lin et al. (Proc. Natl. Acad. Sci. U.S.A., 82, 7580–7585 (1985)), and Recny et al. (J. Biol. Chem., 262, 17156–17161 (1987)). An example of an erythropoietin differing in sugar chain includes that reported by Takeuchi et al. (Proc. Natl. Acad. Sci. U.S.A., 86, 7819–7822 (1989)). An example of an erythropoietin partially lacking in sugar chain includes that reported by Dordal et al. (Endocrinology, 116, 2293–2299 (1985)). An example of a derivative of an erythropoietin includes that reported by Satake et al. (Biochim. Biophys. Acta P, 1038, 125–129 (1990)), in which the charges of the amino acid residues of interest are altered (e.g. amidination, guanidination). In addition, a modification of erythropoietin by conjugating polyethylene glycol can be obtained by the well-known method (Miyata et al., Agri. Biol. Chem., 52, 1575–1581 (1988)).

Hyaluronic acid, which is employed in the present invention, is a mucopolysaccharide consisting of N-acetylglucosamine and glucuronic acid. A nontoxic salt of hyaluronic acid may also be likewise employed. The nontoxic salt includes the salts with alkali metals such as sodium, potassium, etc. and those with alkaline earth metals such as magnesium, calcium and the like. The most preferred salt is the sodium salt for purposes of the invention. Hyaluronic acid or its nontoxic salt preferably have a molecular weight of about $2\times10^5$ to $5\times10^6$ (viscosity method), more preferably about $5\times10^5$ to $3\times10^6$, still more preferably about $7\times10^5$ to $2.5\times10^6$.

While the long-acting composition of the invention contains erythropoietin and hyaluronic acid or its nontoxic salt as mentioned above, the two ingredients are preferably present in the same dosage unit. For example, this is assured when both are dissolved or suspended in sterile water or sterilized saline within the ampule or vial. This procedure may involve mixing erythropoietin with hyaluronic acid or its salt, for example, admixing a solution of erythropoietin with a solution of hyaluronic acid or its nontoxic salt thereof or adding a powder of hyaluronic acid or its nontoxic salt to a solution of erythropoietin or the latter to the former.

The goal of admixing ingredients is preferably in that erythropoietin activity is maintained and bubble formation is minimized during the process. The ingredients are put into a vessel (for example, bottle or drum) either at the same time or in any order. The total volume of the ingredients is preferably at most three quarters, more preferably at most three fifths, further preferably at most half, still more preferably at most one third of the capacity of the vessel. The vessel is shook gently and preferably rotated about its longitudinal axis for rotary blending. The number of revolution is selected according to the combination of the following conditions: the capacity of the vessel, the total volume of the ingredients, the concentration of hyaluronic acid or its nontoxic salt, the temperature of the system, and so on. The preferred number of revolution ranges from 10 round per minute(rpm) through 1000 rpm, although this is not an exclusive range. The atmosphere in the vessel can be sterile clean air or sterile clean nitrogen gas. The resultant erythropoietin-hyaluronic acid solution can be transferred to small vials or ampules, and can be further subjected to lyophilization.

The dosing solution may also be prepared by adding sterile water or sterilized saline to a lyophylisate containing both erythropoietin and hyaluronic acid or its nontoxic salt. Such a dosage unit may contain by further mixing with the common additives such as a pH adjusting agent, local anesthetic agent, solubilizer, isotonizing agent, adsorption inhibitor and so on. Preferred additives are mannitol, sorbitol, sodium chloride, glycine, ammonium acetate, water-soluble protein which does not have any practical pharmacological effect (hereinafter it is sometimes referred to as "water-soluble protein") and so on. Among said additives, water-soluble protein is preferred. The term "pharmacological effect" is defined herein as an hematopoietic effect to cause erythropoiesis.

As the water-soluble protein, it is exemplified by the protein which dissolves in water, saline or buffers and usually have its own solubility.

Specific examples of the water-soluble protein include human serum albumin, human serum globulin, collagen, gelatin.

Examples of said pH adjusting agent include glysine, ammonium acetate, citric acid, hydrochloric acid, sodium hydroxide. Examples of said local anesthetic agent include chlorobutanol, xylocaine hydrochloride. Examples of said solubilizer include glycerol, polyethylene glycol 400. Examples of said isotonizing agent include mannitol, sorbitol, sodium chloride. Examples of said adsorption inhibitor include polyoxyethylene sorbitan monooleate (Tween 80).

The preferred final concentration of hyaluronic acid or sodium hyaluronate in the pharmaceutical composition of the invention is less than one percent from viscosity points of view, namely in terms of the ease of procedures and administration. The more specific desirable concentration range is 0.02 to less than 1% (w/v), more preferably 0.1 to less than 1% (w/v), still more preferably 0.2 to 0.8% (w/v). While the proportion of erythropoietin in the composition should vary with the dosage and cannot be stated in general terms, dosage of the long-acting erythropoietin composition of the present invention for adult human should vary depending on the seriousness of anaemia and ranges preferably from about 100 international units (IU) to about 60000 IU per shot, more preferably from about 1000 IU to about 10000 IU, still more preferably from about 1000 IU to 6000 IU, although this is not an exclusive range and should be left to the prescription by medical doctors. Subcutaneously, generally a large drug volume can be administered but the weight ratio of erythropoietin to hyaluronic acid is dependent on the relationship between the minimum certainly injectable volume and the maximum volume not causing pain to the patient. Although it depends on the specific activity of erythropoietin, the weight ratio of erythropoietin to hyaluronic acid or its nontoxic salt thereof is exemplified as 0.0001:1 through 10:1, preferably 0.0002:1 through 5:1, more preferably 0.0002:1 through 1:1, still more preferably 0.0002:1 through 0.1:1.

The amount of water-soluble protein in the composition of one dosage unit contain is preferably 0.05 mg through 50 mg, more preferably 0.5 mg through 20 mg, still more preferably 0.75 mg through 10 mg. The weight ratio of water soluble protein to hyaluronic acid or its nontoxic salt thereof is preferably 0.001:1 through 100:1, more preferably 0.01:1 through 10:1, still more preferably 0.1:1 through 10:1.

The pH of the pharmaceutical composition of the invention should be such that, within the range tolerable for injection, it does not adversely affect the activity of erythropoietin, alter the viscosity of the solution in any drastic way or tend to form a precipitate. Specifically, the preferred pH range of the composition is pH 4 through pH 8, preferably pH 5 through pH 8, more preferably pH 6 to pH 8.

The viscosity of the present composition, when it is prepared to be a solution, is adjusted preferably to not more than about 500 centipoise (cp), more preferably about 50 to 400 cp. The viscosity depends upon the molecular weight and concentration of hyaluronic acid or its non toxic salt used, the concentration of the water-soluble protein used, the concentration of erythropoietin used, or the concentration of isotonizing agent used, so that the viscosity is adjusted by changing the concentration(s) of the compound(s) used. The values of the viscosity corresponds to those measured by employing Cone LD in E type viscosity meter (TOKIMEC, Japan) at 25° C.

The pharmaceutical composition of the present invention is preferably supplied as a liquid formulation in which erythropoietin and hyaluronic acid or its nontoxic salt are dissolved or dispersed in sterile distilled water or sterile saline. The liquid formulation can contain said excipients such as water-soluble protein. The liquid formulation are maintained at a normal refrigeration range, preferably from about +2° C. to +8° C. In addition, the pharmaceutical composition of the present invention is preferably supplied as a lyophilized formulation which are obtained by lyophilizing the solution or dispersion of erythropoietin and hyaluronic acid or its nontoxic salt. The lyophilized formulation will also have a crystalizing solute and can contain said excipients such as water-soluble protein. The lyophilized formulation are maintained at a temperature range from about −20° C. to about +40° C., preferably from about −5° C. to about 30° C. and more preferably from about +2° C. to about +30° C.

When administering, the lyophilized composition is diluted or dissolved in a pharmaceutically acceptable injectable vehicle such as distilled water for injection, physiological saline for injection.

The pharmaceutical composition of the invention is administered parenterally, namely by injection and particularly by subcutaneous injection. However, other routes of administration, such as intramuscular or intravenous injection, may be adopted depending on intended applications. Since the viscosity of the long-acting pharmaceutical composition of the invention is comparatively low, the composition can be easily aspirated from an ampule or vial into a syringe using a 25 G or 26 G needle. The bubbles that may form during aspiration are readily liquidated as the solution is allowed to stand for a brief time within the syringe.

The efficacy of the present composition, when it is an aqueous injection, is sustainedly exhibited over a time period of not less than 24 hours or longer such as one day through one week. So, since the administration involves a solution, dosage adjustment is easily carried out, and since the efficacy is long enough the present composition can be administered at an interval corresponding to an interval of efficacy assessment.

Thus, the present invention provides a long-acting erythropoietin composition which insures a sustained concentration of erythropoietin within a pharmacologically effective range and features a low concentration of hyaluronic acid or its salt.

Further, the present erythropoietin composition can be supplied in a prefilled syringe for self-administration, since the liquid formulation will not be subject to physical disturbances such as shaking due to its low viscous nature.

Furthermore, in the present invention; the pharmacologically active polypeptide secreted by an animal body means a secretory peptide or protein that is produced in an animal body, and secreted internally to blood stream (endocrine) or to surrounding body fluid (paracrine or autocrine) or externally to the outside of the body (exocrine). In addition, the pharmacologically active polypeptide in the present invention means one that is produced by an animal body either as a natural or genetically engineered occurrence.

In the present invention, animal body means an animal comprising a single eukaryotic cell, an animal comprising multiple eukaryotic cells, or a tissue or organ isolated from the animal.

Examples of said animal comprising a single eukaryotic cell include yeast. Examples of said animal comprising multiple eukaryotic cells include a vertebrate animal, an invertebrate animal. And examples of said tissue or organ isolated from the animal include an cancer cell line derived from human or mouse.

Examples of said vertebrate animal include mammals (e.g. human, rodent (e.g. rat, mouse), bovine, horse, sheep), birds (e.g. poultry (e.g. chicken)), fishes (e.g. salmon, tuna), reptile (e.g. snake). Examples of said invertebrate animal include leach and spider.

In said animal, an animal comprising multiple eukaryotic cells is preferred, and specifically, human, snake, spider and leech are more preferred.

As said polypeptide, one whose partition coefficient measured in octanol over water is below about 0.1 is preferred, and one whose partition coefficient measured in octanol over water is below about 0.05 is more preferred.

As said polypeptide, one having molecular weight of about 200 to 200000 is preferred, and one having molecular weight of about 300 to 90000 is more preferred.

Said polypeptides may be naturally derived ones or ones produced by recombination technique or chemical synthesis.

Examples of the polypeptide include cytokines, peptide hormones, growth factors, the factors that affect cardiovasculr system, cell attachment factors, the factors that affect central and peripheral nerve system, the factors that affect body fluid electrolytes and blood organic constituents, the factors that affect bone and skeltal system, the factors that affect gastro-intestinal system, the factors that affect nephro-urinary system, the factors that affect connective tissues and skins, the factors that affect sensory organs, the factors that affect immune system, the factors that affect respiratory system, the factors that affect genital system, and enzymes.

As the polypeptide, cytokines, peptide hormones, growth factors, the factors that affect cardiovasculr system, the factors that affect central and peripheral nerve system, the factors that affect body fluid electrolytes and blood organic constituents, the factors that affect bone and skeltal system, the factors that affect gastro-intestinal system, the factors that affect immune system, the factors that affect respiratory system, the factors that affect genital system and enzymes are preferred.

Examples of cytokines include lymphokines, monokines and haematopoietic factors.

Examples of lymphokines include interferons (e.g. alpha, beta, gamma) and interleukins (e.g. IL-2 to IL-11).

Examples of monokines include IL-1, tumor necrotizing factor (e.g. TNF alfa and beta), and leukemic inhibitory factors (LIF).

Examples of haematopoietic factors include erythropoietin, granulocyte colony stimulating factors (G-CSF), granulocyte-macrophage colony stimulating factors (GM-SCF), macrophage colony stimulating factors (M-CSF).

Said haematopoietic factors also include ones that have thrombopoietic growth action, e.g., lymphocyte growth factor formulation (Leukoprol, Morinaga Milk, Japan), thrombopoietin, thrombocyte poiesis stimulatory factor, and megakaryocyte potentiator.

Examples of the factors that affect bone and skeltal system include calcitonin, bone GlA peptide, parathyroid hormone or its active fragment, parathyroid hormone related peptide (PTH-rp) or its active fragment (osteostatin, Endocrinology, 129, 324 (1991)) or histone H4-related osteogenic growth peptide (OGP) (The EMBO Journal, 11, 1867(1992)) or muteins of any of them, or derivatives or analogs of any of them.

Examples of growth factors include nerve growth factor (NGF), epidermal growth factor (EGF), fibrobalst growth factor (FGF), insulin like growth factor (IGF), transforming growth factor (TGF), and platelet derived growth factor (PDGF).

Examples of peptide hormone include insulin, growth hormone, leutenizing hormone releasing hormone (LH-RH), adrenocorticotropic hormone (ACTH), amylin, oxytosin, and leutenizing hormone (LH) or derivatives of any of them.

Examples of the factors that affect cardiovascular system include those that control blood pressure and arteriosclerosis such as endothelin, endothelin inhibitor, vasopressin, renin, angiotensin I, angiotensin II, angiotensin III, angiotensin I inhibitor, angiotensin II receptor antagonist and atrial natriuretic peptide (ANP), and antiarrhythmic peptide.

Examples of the factors that affect central and peripheral nerve system include opoid peptides (e.g., enkephalin, endorphin, kyotorphin), neurotropic factor (NTF), calcitonin gene related peptide, pituitary adenylate cyclase activating polypeptide (PACAP), thyrotropin releasing hormone (TRH) and salts and derivatives thereof (Japanese Patent Application Laid-open 121273/1975 corresponding to U.S. Pat. No. 3,959,247 and No. 116465/1977 corresponding to U.S. Pat. No. 4,100,152), and neurotensin.

Examples of the factors that affect gastrointestinal system include secretin and gastrin.

Examples of the factors that affect immune system include those that control inflammation and malignant neoplasm and that attack infective microorganisms.

Examples of the factors that affect body fluid electrolytes and blood organic constituents include those that control blood clotting, plasma cholesterol concentration, and metal ion concentration.

These peptides or factors may further include soluble receptors for the polypeptides.

Examples of cell attachment factors include laminin and inter cellular adhesion molecule (ICAM) 1.

Examples of the polypeptides include natural derived, synthetic or genetically engineered peptides and proteins capable of serving as antigens, e.g., cedar pollen and ragweed pollen. These are administered alone, in a hapten-bound form, or together with an adjuvant in compositions of the present invention, in the form of injections.

Said peptides may further be enzymes of a natural origin or produced by gene recombination techniques, including, but not limited to, superoxidedismutase (SOD), asparaginase and kalikrein, among other administrable enzymes.

These peptides or factors each may include those chemically modified with synthetic polymer such as polyethyleneglycol, natural polymers such as chondroitin, saccharides, or non-peptide substances. Said non-peptide substances may be either ligands for receptors or antigens for antibodies. In addition, the polypeptides or factors each may include hybrid peptides in which multiple peptides are combined by chemical method or by recombination technique.

Among said polypeptides, interferons, interleukins erythropoietin, granulocyte colony stimulating factor (G-CSF), granulocyte-macrophage colony stimulating factor (GM-CSF), macrophage colony stimulating factor (M-CSF), fibroblast growth factor (FGF), tumor necrotizing factor (TNF), parathyroid hormone (PTH), calcitonin, insulin and leutenizing hormore-releasing hormore (LH-RH) are more preferred.

These peptides or factors each may include muteins differing in carbohydrate chain structure, factors having no carbohydrate chain, analogs or homologs derivatives, thereof, and active fragments derived from these, irrespective of their mechanisms of action, whether antagonistic or agonistic.

Examples of the chemically synthesized pharmacologically active substances include those that affect cardiovascular system, those that affect cell attachment, those that affect central and peripheral nerve system, those that affect body fluid electrolytes and blood organic constituents, those that affect bone and skeletal system, those that affect gastrointestinal system, those that affect nephro-urinary system, those that affect connective tissues and skins, those that affect sensory organs, those that affect immune system, those that affect respiratory system, those that affect infective microorganisms, and those that affect genital system.

As the chemically synthesized pharmacologically active substances, those that affect cardiovascular system, those that affect cell attachment, those that affect central and peripheral nerve system, those that affect body fluid electrolytes and blood organic constituents, those that affect bone and skeletal system, those that affect gastro-intestinal system, those that affect immune system, and those that affect infective microorganisms are preferred.

Examples of the chemically synthesized pharmacologically active substances that affect cardiovascular system include anti-hypertensive agents such as calcium antagonist, angiotensin converting enzyme inhibitor, angiotensin II receptor antagonist and potassium channel opener.

Examples of the chemically synthesized pharmacologically active substances that affect cell attachment include RGD (arginine-glysine-asparaginic acid) antagonist.

Examples of the chemically synthesized pharmacologically active substances that affect central and peripheral nerve system include psychopharmaceuticals and antipsychotic agents such as diazepam, anti nausea-vomitting agent and anti-dimentia agents such as benzoquinon derivatives.

Examples of the chemically synthesized pharmacologically active substances that affect body fluid electrolytes and blood organic constituents include those that control blood clotting and plasma cholesterol concentration such as sodium pravastatin.

Examples of the chemically synthesized pharmacologically active substances that affect bone and skeletal system include anti osteoporosis agents such as bis-phosphonates, ipuriflavon, vitamin D3, and antirheumatic agents.

Examples of the chemically synthesized pharmacologically active substances that affect gastrointestinal system includes proton pump inhibitor such as lansoprazol and $H_2$ receptor antagonist such as cimetidine.

Examples of the chemically synthesized pharmacologically active substances that affect immune system include anti-inflammatory agents such as indomethacin, anti tumor agents such as cis-platinum, adriamycin, anti-allergic agents and nonpeptide antigenic substance.

Examples of the chemically synthesized pharmacologically active substances that affect respiratory system include antiasthmatic agent.

Examples of the chemically synthesized pharmacologically active substances that affect infective microorganisms include antiviral agents and antibiotics such as cephalosporin and penicillin.

Examples of the chemically synthesized pharmacologically active substances that affect genital system include sex steroids such as testosteron.

Examples of the chemically synthesized pharmacologically active substances further include hormone (dexamethasone, predonisolone) and non-peptide antigenic substances.

Said chemically synthesized pharmacologically active substances include inorganic and organic ones.

In addition, these may include prostagalndins, leukotrients, saccharides, polysaccharides, metal chelates, or nucleotides such as antisense RNA or DNA.

Said chemically synthesized nonpeptide antigenic substances are administered alone, in a hapten-bound form, or together with an adjuvant in compositions of the present invention, in the form of injections.

In the present specification, the term "hyaluronic acid" includes hyaluronic acid which is a mucopolysaccharide composed of N-acetylglucosamine and glucuronic acid, nontoxic salts thereof, hyaluronic acid derivatives and notoxic salts thereof. The nontoxic salts are, for example, salts with alkali metals, such as sodium and potassium, and salts with alkaline earth metals, such as magnesium and calcium. Among them, the sodium salt is most preferred. Hyaluronic acid and salts thereof preferably have a molecular weight of $1 \times 10^4$ to $5 \times 10^6$ (as determined by the viscosity method using intrinsic viscosity and the Mark-Houvinc equation), more preferably about $1 \times 10^5$ to $3 \times 10^6$.

The water-soluble protein injectable into body fluids without showing any substantial pharmacological activity, which is to be incorporated in the composition of the present invention and which is hereinafter sometimes referred to briefly as "water-soluble protein", includes, among others, serum albumin, globulin, collagen, and gelatin. Among them, serum albumin is preferred. The water-soluble protein is preferred intact with no chemical modification.

The term "pharmacological effect" is defined herein as a substantial pharmacological effect caused by water-soluble protein alone at a concentration used in a single dosage unit form.

The water-soluble composition of this invention is adjusted such that when it is dissolved in water, the aqueous solution has a viscosity of not more than about 500 centipoises (cp), preferably within the range of about 50 to 400 cp. Said viscosity depends on the molecular weight and concentration of hyaluronic acid, the concentration of the water-soluble protein, the concentration of the pharmacologically active substance and the concentration of the salt or salts such as sodium chloride (used as the isotonizing agent to be mentioned later herein), among others, and also depends to some extent on the pH of the water-soluble composition. Therefore, conditions adequate to give the desired water-soluble composition a viscosity within the above range should be selected.

The viscosity referred to herein is measured at a temperature of 25° C. using a viscometer of the type E (TOKIMEC, Japan) with an LD cone.

A preferred range of hyaluronic acid concentration and a preferred range of water-soluble protein concentration in administering the water-soluble composition are mentioned below.

The water-soluble hyaluronic acid concentration at the time of administration should preferably be about 0.01 to 3% (weight to volume), more preferably about 0.05 to 2% (w/v).

When serum albumin, for instance, is used as the water-soluble protein in the composition of the invention, the serum albumin concentration at the time of administration should preferably be about 0.001 to 5% (w/v), more preferably about 0.005 to 2% (w/v). When globulin is used as the water-soluble protein, the globulin concentration at the time of administration should preferably be about 0.001 to 5% (w/v), more preferably about 0.005 to 2% (w/v). When collagen is used as the water-soluble protein, the collagen concentration at the time of administration should preferably be about 0.001 to 1% (w/v), more preferably about 0.005 to 0.2% (w/v). When gelatin is used as the water-soluble protein, the gelatin concentration at the time of administration should preferably be about 0.001 to 1% (w/v), more preferably about 0.005 to 0.5% (w/v).

The pH of a solution prepared from the water-soluble composition of the present invention should be such that said pH will not exert an adverse influence on the activity of the pharmacologically active substance but is within an acceptable range for injections in general and further such that said pH will neither cause a great change in viscosity of the solution nor allow formation of a precipitate or the like. Thus the solution should preferably have a pH of 4 to 8, more preferably a pH of 5 to 8.

As regards the proportion of the pharmacologically active substance in the composition, said substance may be contained therein in an effective amount which may vary depending on the activity of said substance and the therapeutic dose thereof. Generally, the weight ratio between the pharmacologically active substance and hyaluronic acid is preferably from about 0.0001:1 to about 10:1, preferably about 0.0002:1 through about 5:1, more preferably about 0.0002:1 through about 1:1, still more preferably about 0.0002:1 through about 0.1:1. Although any particular mention cannot be made of the proportion of the water-soluble protein, either, said protein can be added in an amount generally employed in injectable pharmaceutical compositions and a preferred weight ratio between the water-soluble protein and hyaluronic acid is about 0.001:1 to about 100:1, more preferably about 0.01:1 through about 10:1, Still more preferably about 0.1:1 through about 10:1.

All the three essential components of the composition of the present invention, namely the pharmacologically active substance, hyaluronic acid and water-soluble protein, are preferably made to occur in a single unit dosage form. Thus, for example, the three are made to occur in an ampule or vial by dissolving or suspending them in sterile water or sterile physiological saline. In this case, the method of preparation may comprise admixing a solution of the pharmacologically active substance, a solution of hyaluronic acid and a solution of the water-soluble protein, or adding hyaluronic acid and the water-soluble protein, each in a powder form, to a solution of the pharmacologically active substance, or any other combination of adequate procedures. The dosage form may also be prepared by adding sterile water or sterile physiological saline to a lyophilizate or vacuum-dried powder in which the pharmacologically active substance, hyaluronic acid and water-soluble protein coexist. This unit dosage form may further contain one or more of conventional additives such as pH adjusting agents (e.g. glycine, hydrochloric acid, sodium hydroxide), local anesthetics (e.g. xylocaine hydrochloride, chlorobutanol), isotonizing agents (e.g. sodium chloride, mannitol, sorbitol), and adsorption inhibitors (e.g. Tween 80).

This unit dosage form may further contain pharmaceutically acceptable excipients such as polyethylene glycol 400 or dextran.

The goal of admixing the ingredients should be such that the activity of the pharmacologically active substance is maintained and bubble formation is minimized during the process. The ingredients are put into a vessel (for example bottle or drum) either at the same time or in any order. The total volume of the ingredients should be at most three quarters, preferably, three fifths, more preferably half, still more preferably one third of the capacity of the vessel. The vessel is shaked gently and preferably rotated about its longitudinal axis for rotary blending. The number of revolution is selected according to the capacity of the vessel, the total volume of the ingredients, the concentration of hyaluronic acid or its non toxic salt, and so on. The preferred number of revolution ranges from 10 round per minute (rpm) through 1000 rpm, although this is not an exclusive range. The atmosphere in the vessel can be sterile clean air or sterile clean nitrogen gas. The resultant solution can be transferred to small vials or ampules, and can be further subjected to lyophilization.

The water-soluble composition of the present invention preferably takes the form of a parenteral preparation.

As said parenteral preparation, there may be mentioned injectable solutions, solutions for transmucosal administration, nasal solutions, otic solutions, etc.

Said injectable solutions include solutions for intravenous administration, for subcutaneous administration, for intraarticular administration, for intramuscular administration and for intraocular administration, among others. Since the viscosity of these long-acting preparations is adjusted to about 500 cp or less, the preparations can be readily drawn from ampules or vials into syringes using a 25G or 26G needle. Bubbles formed upon the drawing can be readily removed by a short period of mere standing.

The liquid form of the composition of the present invention filled in a soft capsule or the lyophilizate powder of the composition of the present invention filled in a hard capsule or compressed to tablet form may be administered to stomach, large intestine, or rectum.

The composition of the present invention may be in a form dissolved in water or in a lyophilized form with a crystalizing solute such as mannitol.

Addition of sterile water or sterile physiological saline to the lyophilizate gives an aqueous solution.

When the composition is in the form of a lyophilizate, it is required that the viscosity of and the component concentrations in the aqueous solution derived therefrom should be within the respective ranges mentioned hereinbefore.

The liquid form or the lyophilizate powder form of the composition of the present invention dissolved or dispersed in a solution of biodegradable polymer such as poly(lactic-glycolic)acid copolymer, poly(hydroxybutyric acid), poly-(hydroxybutyricglycolic) acid copolymer, or the mixture of these can be formulated, for example, to films, microcapsules (microspheres), or nanocapsules (nanospheres) according to the well known methods.

In addition, the composition of the present invention encapsulated in liposomes comprising phospholipids, cholesterols or the derivatives of these according to the well known methods can be further dispersed in physiological saline or the hyaluronic acid solution dissolved in physiological saline.

Further, the composition of the present invention can be supplied in a prefilled syringe for self-administration, since the liquid formulation will not be subject to physical disturbances such as shaking due to its low visous nature.

The composition of the present invention may be maintained at normal temperature or at normal refrigeration range, preferably about 0° C. to a room temperature (e.g. about 25° C.), more preferably from about +2° C. to +8° C.

The doses, target patients and target diseases of the composition of the present invention correspond to those of the pharmacologically active substance.

The water-soluble composition of the present invention is excellent in producing a prolonged effect. Even a low concentration of hyaluronic acid can produce the effect to a satisfactory extent. As a result, a small-gauge needle can be used, whereby pain in patients can be reduced. The composition has a low viscosity and therefore the possibility of bubble formation is much reduced. Thus the composition can be used with ease in clinical practice.

The following working examples and test examples are further illustrative of the present invention but are by no means limitative of the scope of the invention.

Working examples of the invention are presented below.

EXAMPLE 1

Production of Long-Acting Erythropoietin Compositions (1)(a) To one vial of Eposine Injection 3000 (Chugai Pharmaceutical, Japan) containing 3000 IU of erythropoietin (Epoetin Beta), 25 mg of mannitol and 1 mg of human serum albumin was added 2 ml of physiological saline for injection to provide an erythropoietin injection.

(b) To 1.8 ml of the above erythropoietin injection prepared as above (containing 2700 IU of erythropoietin) was added 0.6 ml of a 2% (w/v) physiological saline solution of sodium hyaluronate (average molecular weight 1,470,000 daltons) to provide a long-acting composition of erythropoietin (final concentration of hyaluronic acid 0.5%, w/v).

(2)(a) To one vial of Eposine Injection 3000 (Chugai Pharmaceutical) containing 3000 IU of erythropoietin (Epoetin Beta), 25 mg of mannitol and 1 mg of human serum albumin was added 2 ml of distilled water for injection to provide an erythropoietin injection.

(b) To 1.8 ml of the above erythropoietin injection prepared as above (containing 2700 IU of erythropoietin) was added 0.6 ml of a 2% (w/v) aqueous solution of sodium hyaluronate (average molecular weight 1,470,000 daltons) to provide a long-acting composition of erythropoietin (final concentration of hyaluronic acid 0.5%, w/v).

EXAMPLE 2

A Long-Acting Erythropoietin Composition

The 7-vial equivalent of a human erythropoietin preparation containing 3000 IU human erythropoietin (Epoetin Beta), 25 mg of mannitol and 1 mg of human serum albumin per vial (Eposine Injection 3000, Chugai Pharmaceutical) was dissolved in 1 ml/vial of 25 mM Tris-acetic acid buffer (pH 7.0). Using a Superloop (Pharmacia), 7 ml of this solution was applied to a weak anion exchanger column (Mab Column, J. T. Baker, U.S.A.) connected to an Ultrochrom GTi HPLC system (Pharmacia) and elution was carried out on a linear gradient from 25 mM Tris-acetic acid buffer (pH 7.0) to 2M sodium acetate buffer (pH 6.0). (The flow rate was 0.8 ml/min. and the detection wavelength was 280 nm). The eluate was collected in 1.6 ml fractions using a Super Rack (Pharmacia). The chromatogram obtained is shown in FIG. 3. Test tubes numbered 8 to 11 were pooled and the human erythropoietin in the eluate was assayed by ELISA (EPO-ELISA; Boehringer, Mannheim). It is apparent from FIG. 3 that serum albumin appears as two broad peaks on both sides of the erythropoietin band, indicating a neat resolution from erythropoietin.

To 0.7 ml (26.9 µg) of the human erythropoietin solution thus obtained was added 4 µl of Albumin Nichiyaku (Nippon Seiyaku) containing 20% (w/v) of human serum albumin, followed by addition of 1.4 ml of physiological saline for injection (Fuso Pharmaceutical) to make 2.1 ml. To this solution was added 10.5 mg of sodium hyaluronate (average molecular weight 1,470,000 daltons, Genzyme). The viscosity value was 297 cp.

EXAMPLE 3

A Long-Acting Erythropoietin Composition

A glass vial (capacity: ca. 5 ml) was filled with 0.7 ml (26.9 µg) of the human erythropoietin solution (Epoetin Beta) obtained in Example 2, followed by addition of 0.7 ml of physiological saline (Fuso Pharmaceutical). Then, 0.7 ml of a 1.5% (w/v) solution of sodium hyaluronate (average molecular weight 1,470,000 daltons, Genzyme) in physiological saline for injection was added.

The glass vial (capacity: ca. 5 ml) containing the above solutions was hermetically closed and subjected to rotary blending in a 200 ml egg-plant-type flask equipped with a three-one motor (Heydon) by rotation about its longitudinal axis for about 1 hour (20–100 rpm). The procedure gave a long-acting dosing solution substantially free of bubbles.

EXAMPLE 4

A Long-Acting Erythropoietin Composition

A glass vial (capacity: ca. 5 ml) was filled with 0.7 ml (26.9 µg) of the human erythropoietin solution (Epoetin Beta) obtained in Example 2 followed by addition of 4 µl of Albumin Nichiyaku (Nippon Seiyaku) containing 20% (w/v) of human serum albumin and 0.7 ml of physiological saline for injection (Fuso Pharmaceutical). To this mixture was added 0.7 ml of a 1.5% (w/v) solution of sodium hyaluronate (average molecular weight 1,470,000 daltons, Genzyme) in physiological saline for injection (Fuso Pharmaceutical). The glass vial (capacity: ca. 5 ml) containing these solutions was hermetically closed and subjected to rotary blending in a 200 ml egg-plant-type flask equipped with a three-one motor (Heydon) by rotation (20–100 rpm) about its longitudinal axis for about one hour. The above procedure gave a long-acting dosing solution substantially free of bubbles.

EXAMPLE 5

A Long-Acting Erythropoietin Preparation

In 2 ml of physiological saline for injection was dissolved Eposine Injection 3000 (Chugai Pharmaceutical) containing 3000 IU of erythropoietin (Epoetin Beta), 25 mg of mannitol and 2 mg of human serum albumin to provide an erythropoietin injection. A glass vial (capacity: ca. 5 ml) was filled with 1.5 ml of the above injection, followed by addition of 0.5 ml of a 2% (w/v) solution of sodium hyaluronate (average molecular weight 1,470,000: Genzyme) in physiological saline. The glass vial (capacity: ca. 5 ml) containing these solutions was hermetically closed and subjected to rotary blending by rotation about its longitudinal axis (20–100 rpm) in a 200 ml egg-plant-type flask equipped with a three-one motor (Heydon) for about one hour. The procedure gave a long-acting dosing solution substantially free of bubbles. The above procedure was repeated to provide a required quantity of the long-acting dosing solution.

EXAMPLE 6

A Long-Acting Erythropoietin Composition

In 2 ml of physiological saline for injection was dissolved Eposine Injection 3000 (Chugai Pharmaceutical) containing 3000 IU of erythropoietin (Epoetin Beta), 25 mg of mannitol and 1 mg of human serum albumin to provide an erythropoietin injection. A glass vial (capacity: ca. 5 ml) was filled with 1.7 ml of the above injection and, then, 0.19 ml of a 2% (w/v) solution of sodium hyaluronate (average molecular weight 1,470,000; Genzyme) in physiological saline was added. The glass vial (capacity: ca. 5 ml) containing these solutions was hermetically closed and subjected to rotary blending by rotation about its longitudinal axis (20–100 rpm) in a 200 ml egg-plant-type flask equipped with a three-one motor (Heydon) for about one hour. The procedure gave a long-acting dosing solution substantially free of bubbles.

EXAMPLE 7

A Long-Acting Erythropoietin Composition

A glass vial (capacity: ca. 5 ml) was filled with 1.3 ml of Espo Injection (Kirin Brewery), a human erythropoietin preparation containing 3000 IU of erythropoietin (Epoetin Alpha) and 5 mg of human serum albumin, followed by addition of 1.3 ml of Artz, a sodium hyaluronate preparation (average molecular weight: ca. 800,000–900,000, Seikagaku Kogyo, Japan). The glass vial (capacity: ca. 5 ml) containing these solutions was hermetically closed and subjected to rotary blending in a 200 ml egg-plant-type flask equipped with a three-one motor (Heydon) by rotation about its longitudinal axis (20–100 rpm) for about 1 hour. The procedure gave a long-acting dosing solution substantially free of bubbles.

EXAMPLE 8

A Long-Acting Erythropoietin Composition

A glass vial (capacity: ca. 5 ml) was filled with 1.4 ml of Espo Injection (Kirin Brewery), a human erythropoietin preparation containing 3000 IU of erythropoietin (Epoetin Alpha) and 5 mg of human serum albumin, followed by addition of 0.7 ml of a 1.5% (w/v) solution of sodium hyaluronate (average molecular weight: ca. 500,000) in physiological saline. The glass vial (capacity: ca. 5 ml) containing these solutions was hermetically closed and subjected to rotary blending in a 200 ml egg-plant-type flask equipped with a three-one motor (Heydon) by rotation about its longitudinal axis (20–100 rpm) for about 1 hour. The procedure gave a long-acting dosing solution substantially free of bubbles.

EXAMPLE 9

A Long-Acting Erythropoietin Composition

A glass vial (capacity: ca. 5 ml) was filled with 1.4 ml of Espo Injection (Kirin Brewery), a human erythropoietin preparation containing 3000 IU of erythropoietin (Epoetin Alpha) and 5 mg of human serum albumin, followed by addition of 0.7 ml of a 1.5% (w/v) solution of sodium hyaluronate (average molecular weight: 1,470,000, Genzyme) in physiological saline. The glass vial (capacity: ca. 5 ml) containing these solutions was hermetically closed and subjected to rotary blending in a 200 ml egg-plant-type flask equipped with a three-one motor (Heydon) by rotation about its longitudinal axis (20–100 rpm) for about 1 hour. The procedure gave a long-acting dosing solution substantially free of bubbles.

EXAMPLE 10

A Long-Acting Erythropoietin Composition

A glass vial (capacity: ca. 5 ml) was filled with 1.4 ml of Espo Injection (Kirin Brewery), a human erythropoietin preparation containing 3000 IU of erythropoietin (Epoetin Alpha) and 5 mg of human serum albumin, followed by addition of 0.7 ml of a 0.9% (w/v) solution of sodium hyaluronate (average molecular weight: 2,300,000) in physiological saline. The glass vial (capacity: ca. 5 ml) containing these solutions was hermetically closed and subjected to rotary blending in a 200 ml flask equipped with a three-one motor (Heydon) by rotation about its longitudinal axis (20–100 rpm) for about 2 hours. The procedure gave a long-acting dosing solution substantially free of bubbles.

EXAMPLE 11

A Long-Acting Erythropoietin Composition

A glass vial (capacity: ca. 5 ml) was filled with 1.3 ml of Espo Injection (Kirin Brewery), a human erythropoietin preparation containing 3000 IU of erythropoietin (Epoetin Alpha) and 5 mg of human serum albumin, followed by addition of 1.3 ml of a 1.5% (w/v) solution of sodium hyaluronate (average molecular weight: 1,470,000, Gemzyme) in physiological saline. The glass vial (capacity: ca. 5 ml) containing these solutions was hermetically closed and subjected to rotary blending in a 200 ml flask equipped with a three-one motor (Heydon) by rotation about its longitudinal axis (20–100 rpm) for about 2 hours. The procedure gave a long-acting dosing solution substantially free of bubbles.

Experimental Example 1

Comparative Composition 1: Physiological saline for injection, 2 ml.

Comparative Composition 2: To one vial of Eposine Injection 3000 (Chugai Pharmaceutical) containing 3000 IU of erythropoietin (Epoetin Beta), 25 mg of mannitol and 1 mg of human serum albumin was added 2 ml of physiological saline for injection to provide an erythropoietin injection.

The composition Example 1(1)(b) and Comparative Composition 2 were respectively administered twice at an interval of one week, each dose corresponding to a 7-day dosage based on 135 IU of erythropoietin/kg/day, subcutaneously at the back of 8-week-old male SD rats. As a negative control, Comparative Composition 1, physiological saline for injection, was similarly administered. Before administration and at timed intervals after administration, about 0.4 ml portions of blood were drawn into microhematocrit capillary tubes (Dramont Scientific) and the hematocrit level was determined (KH120M centrifuge, Kubota).

Figure 1:
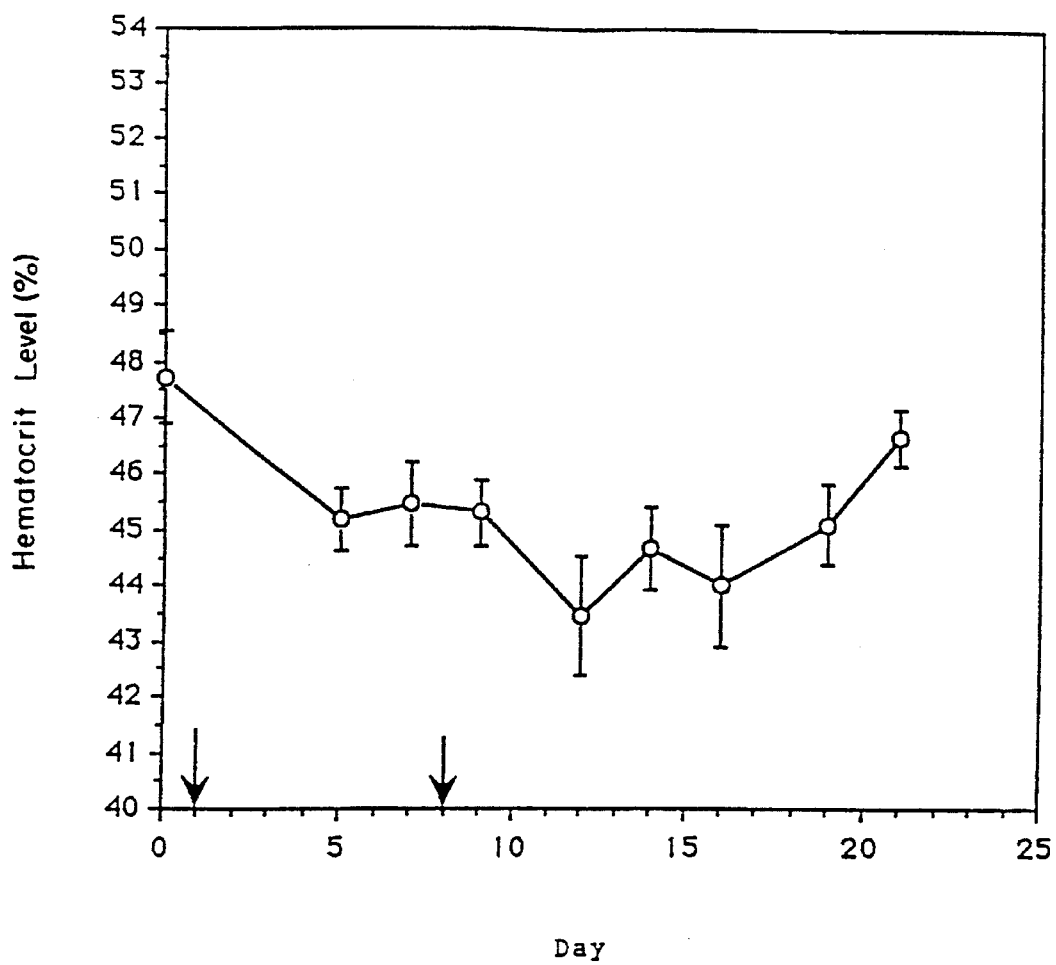
FIG. 1 is a diagrammatic representation, obtained in Experimental Example 1, of the time course of hematocrit level which prevailed when Comparative Composition 1 (physiological saline) was administered twice at an interval of one week.
Figure 2:
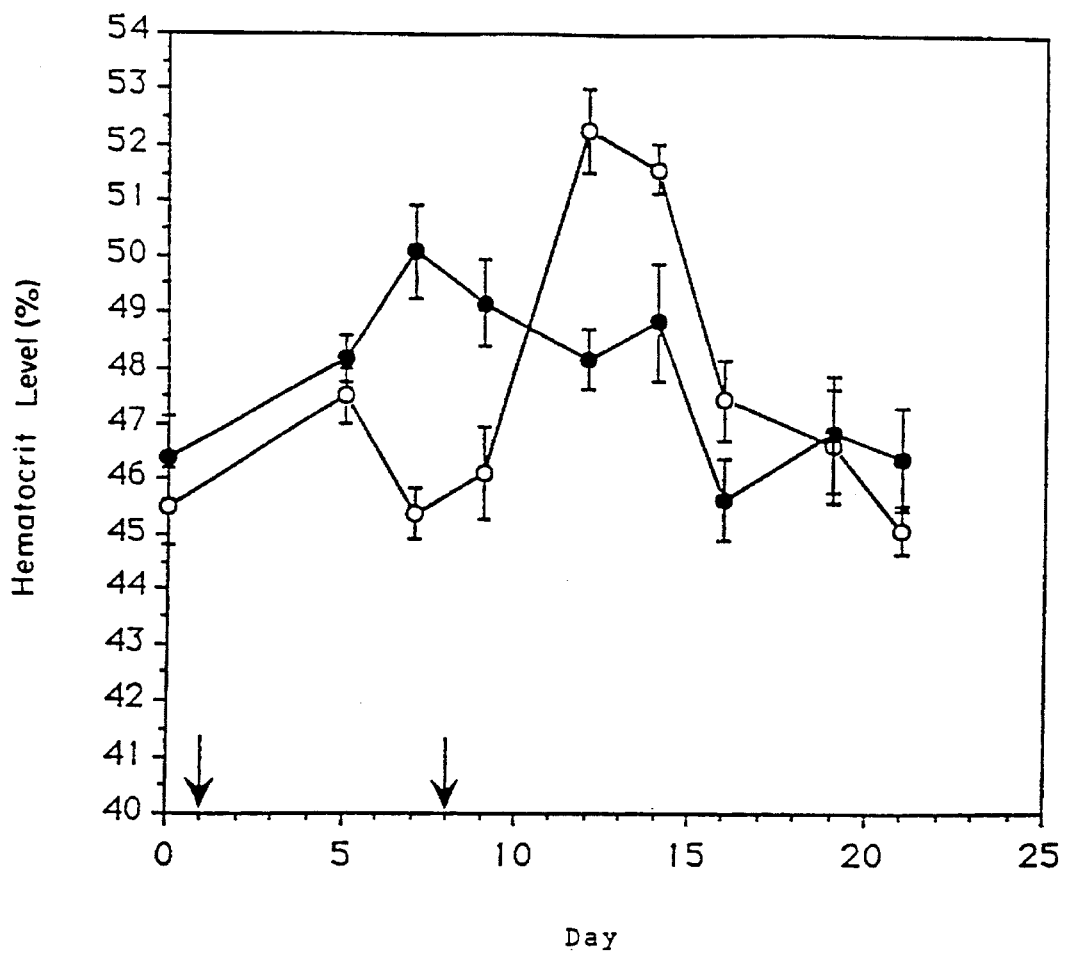
FIG. 2 is a diagrammatic representation, obtained in Experimental Example 1, of the time course (open circles) of hematocrit level which prevailed when the erythropoietin injection (Comparative Composition 2) was administered twice at an interval of one week and the time course (solid circles) of hematocrit level which prevailed when the erythropoietin injection (Example 1 (1)(b)) was administered twice at an interval of one week.

The results are plotted in FIGS. 1 and 2. The saline group showed no increase in hematocrit level but rather showed a transient decrease in hematocrit level due to blood collection (FIG. 1). With Comparative Composition 2, some elevation of hematocrit level was found 5 days after the first dose but the hematocrit level fell back on day 7 and a sharp rise of hematocrit level occurred after the second dose (FIG. 2, open circles). On the other hand, with the Composition of Example 1(1)(b), the hematocrit level rose gradually on days 5 to 7 after the first dose and maintained a substantial plateau till 2 weeks after initiation of the experiment, with the second dose intervening (FIG. 2, solid circles). This suggests that the humoral concentration of erythropoietin is sustained and controlled within the pharmacologically effective range. An abrupt elevation of hematocrit level is undesirable and any behavior of hematocrit level that is typically portrayed in FIG. 2 (open circles) is objectionable. From this point of view, too, it is clear that the Composition of Example 1(1)(b) is an excellent long-acting preparation of erythropoietin.

Experimental Example 2

Comparative Composition 3: To 0.7 ml of a solution of human erythropoietin (26.9 µg) as prepared in Example 2 was added 1.4 ml of physiological saline (Fuso Pharmaceutical) for injection to make 2.1 ml. Then, 1.5 mg of sodium hyaluronate (average molecular weight 1,470,000 daltons; Genzyme) was added to the mixture.
Comparative Composition 4: Physiological saline for injection, 2 ml.

The composition of Example 2 and Comparative Composition 3, both for injection, were respectively administered subcutaneously at the back of 8-week-old male SD rats in the 7-day equivalent dose of 1.83 µg/kg/day twice one week apart. As a control, Comparative Composition 4, i.e. physiological saline for injection, was similarly administered. Before administration and serially after administration, about 0.4 ml of blood was withdrawn (EDTA•2 Na added as anticoagulant) into a microhematocrit capillary tube (Dramont Scientific) and the hematocrit level was determined (KH120M centrifuge, Kubota). The results are plotted in FIG. 4. FIG. 4 is a diagram showing the time courses of hematocrit level as found when Comparative Composition 3 (open squares), Comparative Composition 4 (open circles) and Erythropoietin Composition of Example 2 (solid circles) were administered twice one-week apart. In the group treated with Comparative Composition 4, i.e. physiological saline, the hematocrit level was not elevated but remained almost unchanged. As to Comparative Composition 3 vs. Composition of Example 2, the hematocrit level rose after the first dose in both groups. After the second dose, however, the hematocrit level remained higher up to day 14 after administration in the group treated with the composition of Example 2 than in the group treated with Comparative Composition 3. The above results indicate that although an erythropoietin-hyaluronate system gives a sustained erythropoietin effect, addition of Serum albumin to the same system potentiates the pharmacologic effect with the same amounts of erythropoietin and hyaluronate.

Experimental Example 3

An injection was prepared according to the following formula and tested.
Comparative Composition 5: To 0.7 ml (26.9 µg) of the human erythropoietin (Epoetin Beta) mentioned above was added 1.4 ml of physiological saline for injection (Fuso Pharmaceutical) to make 2.1 ml.
Comparative Composition 6: Physiological saline for injection, 2 ml.

The injectable composition of Example 3 and Comparative Composition 5 were respectively administered subcutaneously at the back of 8-week-old male SD rats in the 7-day equivalent dose of 0.549 µg/rat/day. As a control, Comparative Composition 6, i.e. physiological saline, was similarly administered. Before administration and serially after administration, about 0.4 ml of blood was withdrawn (anticoagulant EDTA•2 Na) into a microhematocrit capillary tube (Dramont Scientific) and the hematocrit level was determined (KH120M centrifuge, Kubota).

In the group treated with Comparative Composition 6, i.e. physiological saline, the hematocrit level did not rise but remained almost unchanged. FIG. 5 shows the results of administration of the composition of Example 3 (solid circles) and Comparative Composition 5 (open circles). In the group treated with the composition of Example 3, the hematocrit level rose gradually following administration, reached a peak on day 5 and, then, declined somewhat on day 7. In the group treated with Comparative Composition 5, the hematocrit level was elevated following administration but the elevation was not as great as in the group treated with the composition of Example 3. The above results indicate that an erythropoietin-hyaluronate system insures a sustained erythropoietin effect with a minimal variation of hematocrit.

Experimental Example 4

An injection was prepared according to the following formula and tested.
Comparative Composition 7: Eposine Injection 3000 (Chugai Pharmaceutical) containing 3000 IU of erythropoietin (Epoetin Beta), 25 mg of mannitol and 1 mg of human serum albumin was dissolved in 2 ml of physiological saline for injection to provide an erythropoietin injection.
Comparative Composition 8: Physiological saline for injection, 2 ml.

The composition of Example 5 and Comparative Composition 7 were respectively administered subcutaneously at the back of 8-week-old SD rats in the 7-day equivalent dose of 121.5 IU/rat/day twice one week apart. As a control, Comparative Composition 6, i.e. physiological saline, was similarly administered. Before administration and serially after administration, about 0.4 ml of blood was withdrawn (EDTA•2 Na added as anticoagulant) into a microhematocrit capillary tube (Dramont Scientific) and the hematocrit level was determined (KH120M centrifuge, Kubota).

In the saline group treated with Comparative Composition 8, the hematocrit level was not elevated but remained almost unchanged. FIG. 6 shows the time courses of hematocrit level after administration of the composition of Example 5 (solid circles) and Comparative Composition 7 (open circles). In the group given the composition of Example 5 vs. the group given Comparative Composition 7, both groups showed elevations of hematocrit level but the increase was less prominent in the latter group. After the second dose, whereas the hematocrit level in the group given the composition of Example 5 showed a substantial plateau till day 14, the group given Comparative Composition 7 showed a major upsurge in hematocrit level again. The above results suggest that an erythropoietin-hyaluronate system insures a sustained erythropoietin effect with a reduced variation in hematocrit level.

Experimental Example 5

An injection was prepared according to the following formula and tested.

Comparative Composition 9: Eposine Injection 3000 (Chugai Pharmaceutical) containing 3000 IU of erythropoietin (Epoetin Beta), 25 mg of mannitol and 1 mg of human serum albumin was dissolved in 2 ml of physiological saline for injection to provide an erythropoietin injection.

Comparative Composition 10: Physiological saline for injection, 2 ml.

The composition of Example 5 and Comparative Composition 9 were respectively administered subcutaneously at the back of 8-week-old male SD rats in the 7-day equivalent dose of 18 IU/rat/day twice one week apart. As a control, Comparative Composition 10 was similarly administered. Before administration and serially after administration, about 0.4 ml of blood was withdrawn (EDTA. 2Na added as anticoagulant) into a microhematocrit capillary tube (Dramont Scientific) and the hematocrit level was determined (KH120M centrifuge, Kubota).

In the saline group treated with Comparative Composition 10, the hematocrit level was not elevated but remained almost unchanged. FIG. 7 shows the time courses of hematocrit level after administration of the composition of Example 5 (solid circles) and Comparative Composition 9 (open circles). In the group given the composition of Example 5 vs. the group given Comparative Composition 9, the hematocrit level rose after the first dose in both groups but the elevation was less pronounced in the latter group. After the second dose, the hematocrit level in the group given the composition of Example 5 rose more gradually, peaked on day 12 after administration and then declined gradually. In the group treated with Comparative Composition 9, the hematocrit level after the second dose rose rapidly, peaked on day 10 and, then, declined gradually. At all observation time points, the hematocrit level was lower in this group than in the group given the composition of Example 5. The above results indicate that an erythropoietin-hyaluronate system insures a sustained erythropoietin effect with reduced variation.

Experimental Example 6

An injection was prepared according to the following formula and tested.

Comparative Composition 11: Eposine Injection 3000 (Chugai Pharmaceutical) containing 3000 IU of erythropoietin (Epoetin Beta), 25 mg of mannitol and 1 mg of human serum albumin was dissolved in 2 ml of physiological saline for injection to provide an erythropoietin injection.

Comparative Composition 12: Physiological saline for injection, 2 ml.

The composition of Example 6 and Comparative Composition 11 were respectively administered subcutaneously at the back of 8-week-old male SD rats in the 7-day equivalent dose of 40.5 IU/rat/day twice, one week apart. As a control, Comparative Composition 12, i.e. physiological saline, was similarly administered. Before administration and serially after administration, about 0.4 ml of blood was withdrawn (EDTA•2 Na added as anticoagulant) into a microhematocrit capillary tube (Dramont Scientific) and the hematocrit level was determined (KH120M centrifuge, Kubota).

In the saline group treated with Comparative Composition 12, the hematocrit level was not elevated but remained almost unchanged. FIG. 8 shows the time courses of hematocrit level after administration of the composition of Example 6 (solid circles) and Comparative Composition 11 (open circles). Both the group given the composition of Example 6 and the group given Comparative Composition 11 showed elevations of hematocrit level but the increase was less prominent in the latter group, which showed a downturn as early as day 7. After the second dose, whereas the hematocrit level in the group treated with the composition of Example 6 continued to rise gradually till day 12, the hematocrit level in the group given comparative Composition 11 increased slowly at first and sharply thereafter. The above results indicate that an erythropoietin-hyaluronate system insures a sustained erythropoietin effect with reduced variation.

Experimental Example 7

An injection was prepared according to the following formula and tested.

Comparative Composition 13: Espo Injection 3000 (Kirin Brewery), a human erythropoietin preparation containing 3000 IU of erythropoietin (Epoetin Alpha) and 5 mg of human serum albumin.

Comparative Composition 14: Physiological saline for injection, 2 ml.

The composition of Example 7 and Comparative Composition 13 were respectively administered subcutaneously at the back of 7-week-old male SD rats in the 7-day equivalent dose of 40.5 IU/rat/day twice, one week apart. As a control, Comparative Composition 14, i.e. physiological saline, was similarly administered. Before administration and serially after administration, about 0.4 ml of blood was withdrawn (EDTA•2 Na added as anticoagulant) into a microhematocrit capillary tube (Dramont Scientific) and the hematocrit level was determined (KH120M centrifuge, Kubota).

In the saline group treated with Comparative Composition 14, the hematocrit level was not elevated but remained almost unchanged. FIG. 9 shows the time courses of hematocrit level after administration of the composition of Example 7 (solid circles) and Comparative Composition 13 (open circles). In the group given the composition of Example 7 vs. the group given Comparative Composition 13, both groups showed elevations of hematocrit level but the increase was less prominent in the latter group. After the second dose, whereas the hematocrit level in the group given the composition of Example 7 showed a substantial plateau till day 14, the hematocrit level in the group given Comparative Composition 13 rose slowly at first and sharply thereafter. The above results indicate that an erythropoietin-hyaluronate system insures a sustained erythropoietin effect with reduced variation.

Experimental Example 8

An injection was prepared according to the following formula and tested.

Comparative Composition 15: Espo Injection 3000 (Kirin Brewery), a human erythropoietin preparation containing 3000 IU of erythropoietin (Epoetin Alpha) and 5 mg of human serum albumin.

Comparative Composition 16: Physiological saline for injection, 2 ml.

The composition of Example 9 and Comparative Composition 15 were respectively administered subcutaneously at the back of 7-week-old male SD rats in the 7-day equivalent dose of 40.5 IU/rat/day twice, one week apart. As a control, Comparative Composition 16, i.e. physiological saline, was similarly administered. Before administration and serially after administration, about 0.4 ml of blood was withdrawn (EDTA·2 Na added as anticoagulant) into a microhematocrit capillary tube (Dramont Scientific) and the hematocrit level was determined (KH120M centrifuge, Kubota).

In the saline group treated with Comparative Composition 16, the hematocrit level was not elevated but remained almost unchanged. FIG. 10 shows the time courses of hematocrit level after administration of the composition of Example 9 (solid circles) and Comparative Composition 15 (open circles). In the group given the composition of Example 9 vs. the group given Comparative Composition 15, both groups showed elevations of hematocrit level but the increase was less prominent in the latter group. After the second dose, the hematocrit level in the group given the composition of Example 9 showed a substantial plateau till day 12, and, then, declined gradually. In the group given Comparative Composition 15, however, the hematocrit level after the second dose continued to rise, peaked on day 12, then, declined. The above results indicate that an erythropoietin-hyaluronate system minimizes the variation of erythropoietin effect and, yet, insures a sustained effect.

Experimental Example 9

An injection was prepared according to the following formula and tested.
Comparative Composition 17: Espo Injection 3000 (Kirin Brewery), a human erythropoietin preparation containing 3000 IU of erythropoietin (Epoetin Alpha) and 5 mg of human serum albumin.
Comparative Composition 18: Physiological saline for injection, 2 ml.

The composition of Example 10 and Comparative Composition 17 were respectively administered subcutaneously at the back of 7-week-old male SD rats in the 7-day equivalent dose of 40.5 IU/rat/day. As a control, Comparative Composition 18, i.e. physiological saline, was similarly administered. Before administration and serially after administration, about 0.4 ml of blood was withdrawn (EDTA 2 Na added as anticoagulant) into a microhematocrit capillary tube (Dramont Scientific) and the hematocrit level was determined (KH120M centrifuge, Kubota).

In the group treated with Comparative Composition 18. i.e. physiological saline, the hematocrit level was not elevated but remained nearly constant. In the group given the composition of Example 10 vs. the group given Comparative Composition 17, the hematocrit level rose after administration in both groups but the increase was less pronounced in the group treated with Comparative Composition 17.

|  | Hematocrit (%) | |
|---|---|---|
|  | Before administration | Day 5 |
| Composition of Example 10 | 39.4 | 43.0 |
| Comparative Composition 17 | 40.3 | 41.1 |

The above results indicate that an erythropoietin-hyaluronate system insures a sustained erythropoietin effect.

Experimental Example 10

An injection was prepared according to the following formula and tested.
Comparative Composition 19: Espo Injection 3000 (Kirin Brewery), a human erythropoietin preparation containing 3000 IU of erythropoietin (Epoetin Alpha) and 5 mg of human serum albumin.
Comparative Composition 20: Physiological saline for injection, 2 ml.

The composition of Example 11 and Comparative Composition 19 were respectively administered subcutaneously at the back of 7-week-old male SD rats in the 7-day equivalent dose of 40.5 IU/rat/day. As a control, Comparative Composition 20, i.e. physiological saline, was similarly administered. Before administration and serially after administration, about 0.4 ml of blood was withdrawn (EDTA·2 Na added as anticoagulant) into a microhematocrit capillary tube (Dramont Scientific) and the hematocrit level was determined (KH120M centrifuge, Kubota).

In the group treated with Comparative Composition 20. i.e. physiological saline, the hematocrit was not elevated but remained nearly constant. The hematocrit levels after administration of the composition of Example 11 and Comparative Composition 19 are shown below.

|  | Hematocrit (%) | |
|---|---|---|
|  | Before administration | Day 5 |
| Composition of Example 11 | 40.5 | 46.1 |
| Comparative Composition 19 | 40.3 | 41.1 |

In the group given the composition of Example 11 vs. the group given Comparative Composition 19, the hematocrit level rose in both groups but less prominently in the latter group. These results indicate that an erythropoietin-hyaluronate system insures a sustained erythropoietin effect.

EXAMPLE 12

Sustained-Release Preparation Containing Basic Fibroblast Growth Factor Muteine

To 0.36 milliliter of a solution of recombinant human basic FGF muteine CS23 (hereinafter sometimes referred to as rhbFGF muteine CS23) (EP-281,822) (0.96 milligram protein/milliliter) were added 1.26 milliliters of physiological saline for injection and 8.1 milligrams of sodium hyaluronate (average molecular weight 1,470,000 daltons; Genzyme, U.S.A.), followed by further addition of 6 microliters of Albumin Nichiyaku (Nihon Pharmaceutical, Japan), a 20% solution of human serum albumin. Viscosity: 366 cp.

EXAMPLE 13

To 0.7 milliliter of physiological saline containing 10 micrograms of nerve cell growth factor (NGF) (Biomedical Technology, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin, Japan) to make the whole volume 2.1 milliliters. To this solution was added 10.5 milligrams of sodium hyaluronate (average molecular weight 1,470,000 daltons; Genzyme). Viscosity: 285 cp.

EXAMPLE 14

To 0.7 milliliter of physiological saline containing 10 micrograms of epithelial growth factor (EGF) (Chemi-Con International, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 305 cp.

EXAMPLE 15

To 0.7 milliliter of physiological saline containing 10 micrograms of insulin-like growth factor (IGF) (Chemi-Con International) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 298 cp.

EXAMPLE 16

To 0.7 milliliter of physiological saline containing 10,000 international units of interferon alpha (Lee Biomolecular Research Labo, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 312 cp.

EXAMPLE 17

To 0.7 milliliters of physiological saline containing 10,000 international units of interferon beta (Pesel, Germany) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 320 cp.

EXAMPLE 18

To 0.7 milliliter of physiological saline containing 10,000 international units of interferon gamma (Genzyme, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 311 cp.

EXAMPLE 19

To 0.7 milliliter of physiological saline containing 10 micrograms of interleukin 2 (IL-2) (produced by the method described in Japanese Patent Application Laid-open No. 78799/1986 corresponding to EP-176,299 and purified by the method described in Japanese Patent Application Laid-open No. 115528/1985 corresponding to EP-145,390; mixture of N-terminal Met-containing species and N-terminal Met-free species) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 320 cp.

EXAMPLE 20

To 0.7 milliliter of physiological saline containing 1 microgram of transforming growth factor (TGF-$\beta$) (Wako Pure Chemical Industries, Japan) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 353 cp.

EXAMPLE 21

To 0.7 milliliter of physiological saline containing 10 micrograms of parathyroid hormone (PTH) (Bachem Fine Chemicals, Switzerland) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 251 cp.

EXAMPLE 22

To 0.7 milliliter of physiological saline containing 5,000 units of granulocyte-macrophage colony stimulating factor (GM-CSF) (ICN Biomedicals, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 301 cp.

EXAMPLE 23

To 0.7 milliliter of physiological saline containing 5,000 units of macrophage colony stimulating factor (M-CSF) (ICN Biomedicals) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 299 cp.

EXAMPLE 24

To 0.7 milliliter of physiological saline containing 1 microgram of acid fibroblast growth factor (FGF-$\alpha$) (Toyobo, Japan) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 274 cp.

EXAMPLE 25

To 1 microgram of tumor necrosis factor (TNF-α) (Wako Pure Chemical, Japan) was added 0.7 milliliter of physiological saline for injection (Fuso Yakuhin). To the mixture was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 286 cp.

EXAMPLE 26

To 0.7 milliliter of physiological saline containing 400 units of Serratia-derived superoxide dismutase (SOD) (Japanese Patent Application Laid-open No. 29285/1982 corresponding to EP-45,222 and No. 16685/1983 corresponding to EP-70,656) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 291 cp.

EXAMPLE 27

To 0.7 milliliter of physiological saline containing 10 micrograms of vasopressin (Cambridge Research Biochemical, Great Britain) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 220 cp.

EXAMPLE 28

To 0.7 milliliter of physiological saline containing 10 micrograms of somatostatin (Bachem Fine Chemicals) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 249 cp.

EXAMPLE 29

To 0.7 milliliter of physiological saline containing 10 micrograms of oxytocin (Bachem Fine Chemicals) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 253 cp.

EXAMPLE 30

To 0.7 milliliter of physiological saline containing luteinizing hormone releasing hormone (LH-RH) (Bachem Fine Chemicals) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 241 cp.

EXAMPLE 31

To 0.7 milliliter of physiological saline containing 10 micrograms of growth hormone releasing factor (Bachem Fine Chemicals) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 265 cp.

EXAMPLE 32

To 0.7 milliliter of physiological saline containing 10 micrograms of growth hormone (UCB Bioproducts, Belgium) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 293 cp.

EXAMPLE 33

To 0.7 milliliter of physiological saline containing 10 micrograms of calcitonin (UCB Bioproducts) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 238 cp.

EXAMPLE 34

To 0.7 milliliter of physiological saline containing 10 micrograms of calcitonin gene-related peptide (UCB Bioproducts) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 229 cp.

EXAMPLE 35

To 0.7 milliliter of physiological saline containing 10 micrograms of brain natriuretic peptide (Peptide Institute, Japan) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 241 cp.

EXAMPLE 36

To 0.7 milliliter of physiological saline containing 10 micrograms of atrial natriuretic peptide (Cambridge Research Biochemicals, U.K.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 243 cp.

EXAMPLE 37

To 0.7 milliliter of physiological saline containing 10 micrograms of an osterocalcin analog (American Peptide, U.S.A.) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 265 cp.

EXAMPLE 38

To 0.7 milliliter of physiological saline containing 10 micrograms of hepatocyte growth factor (Peptide Institute, Japan) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 271 cp.

EXAMPLE 39

To 0.7 milliliter of physiological saline containing urokinase (Nippon Chemical Research, Japan) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 311 cp.

EXAMPLE 40

To 0.7 milliliter of physiological saline containing 10 micrograms of tissue plasminogen activator (TPA) (Bioscot, Great Britain) was added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 335 cp.

EXAMPLE 41

To 0.7 milliliter of physiological saline containing 1 microgram of interleukin 3 (IL-3) (R&D Systems, U.S.A.) is added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 259 cp.

EXAMPLE 42

To 0.7 milliliter of physiological saline containing 1 microgram of interleukin 4 (IL-4) (R&D Systems) is added 4 microliters of Albumin Nichiyaku (Nihon Pharmaceutical) containing human serum albumin at a concentration of 20%, followed by further addition of 1.4 milliliters of physiological saline for injection (Fuso Yakuhin, Japan) to make the whole volume 2.1 milliliters. To this solution was added 10.5 milligrams of sodium hyaluronate (average molecular weight 1,470,000 daltons; Genzyme). Viscosity: 265 cp.

EXAMPLE 43

To 0.7 milliliter of physiological saline containing 1 microgram of interleukin 5 (IL-5) (Amgen, U.S.A.) is added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 282 cp.

EXAMPLE 44

To 0.7 milliliter of physiological saline containing 1 microgram of interleukin 6 (IL-6) (Amgen) is added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 249 cp.

EXAMPLE 45

To 0.7 milliliter of physiological saline containing 1 microgram of interleukin 7 (IL-7) (Genzyme) is added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 255 cp.

EXAMPLE 46

To 0.7 milliliter of physiological saline containing 1 microgram of interleukin 8 (IL-8) (Genzyme) is added 4 microliters of Albumin Nichiyaku (Nihon Pharmaceutical) containing human serum albumin at a concentration of 20%, followed by further addition of 1.4 milliliters of physiological saline for injection (Fuso Yakuhin) to make the whole volume 2.1 milliliters. To this solution was added 10.5 milligrams of sodium hyaluronate (average molecular weight 1,470,000 daltons; Genzyme). Viscosity: 263 cp.

EXAMPLE 47

Long-Acting Insulin Preparation

Three milligrams of pig insulin (26.8 units/milligram; Diosynth, Netherlands) was dissolved in 1.5 milliliters of 0.1N hydrochloric acid and then 1.65 milliliters of physiological saline for injection was added, followed by addition of 15.75 milligrams of sodium hyaluronate (average molecular weight 1,470,000 daltons; Genzyme). To the thus-obtained solution was added 4 microliters of Albumin Nichiyaku (Nihon Pharmaceutical) containing human serum albumin at a concentration of 20%. Viscosity: 384 cp.

EXAMPLE 48

Long Lasting Preparation Containing Granulocyte Colony Stimulating Factor (G-CSF)

To 0.0466 milliliter of a human granulocyte colony stimulating factor preparation (Nupogen; Amgen, U.S.A.) containing, per milliliter, 300 micrograms of recombinant human G-CSF, 50 milligrams of mannitol and 0.004% of Tween 80 was added 4.154 milliliters of physiological saline for injection, followed by further addition of 21 milligrams of sodium hyaluronate (average molecular weight 1,470,000 daltons; Genzyme). To the thus-obtained solution was added 8 microliters of Albumin Nichiyaku (Nihon Pharmaceutical) containing human serum albumin at a concentration of 20%. Viscosity: 264 cp.

EXAMPLE 49

Long-Acting Insulin Preparation

Three milligrams of pig insulin (26.8 units/milligram; Diosynth) was dissolved in 1.5 milliliters of 0.1N hydrochloric acid and then 1.65 milliliters of physiological saline for injection was added, followed by further addition of 15.75 milligrams of sodium hyaluronate (average molecular weight 1,470,000 daltons; Genzyme). To the solution obtained was added 0.5 milligram of human immunoglobulin G (Cappel). viscosity: 328 cp.

EXAMPLE 50

Long-Acting Granulocyte Colony Stimulating Factor (G-CSF) Preparation

To 0.0233 milliliters of a human granulocyte colony stimulating factor preparation (Nupogen; Amgen, U.S.A.) containing, per milliliter, 300 micrograms of a recombinant human G-CSF, 50 milligrams of mannitol and 0.004% of Tween 80 was added 1.377 milliliters of physiological saline for injection, followed by further addition of 8 microliters of Albumin Nichiyaku (Nippon Seiyaku) containing 20% of human serum albumin. To the resultant mixture was added 0.7 milliliter of a 1.5% (w/v) solution of sodium hyaluronate (average molecular weight: 1,470,000 daltons; Genzyme, U.S.A.) in physiological saline for injection (Fuso Pharmaceutical). A glass vial (capacity: ca. 5 milliliters) containing these solutions was tightly stoppered and rotated, for rotary blending, in a 200-milliliter eggplant-shaped flask equipped with a three-one motor (Heydon, Japan) about its longitudinal axis (20–100 revolutions per minute (rpm)) for about one hour. The above procedure gave a long-acting dosing solution substantially free of bubbles.

EXAMPLE 51

To 0.023 milliliter of a human granulocyte colony stimulating factor preparation (Nupogen; Amgen) containing, per milliliter, 300 micrograms of a recombinant human G-CSF, 50 milligrams of mannitol and 0.004% of Tween 80 was added 1.377 milliliters of physiological saline for injection, followed by further addition of 4 microliters of Albumin Nichiyaku (Nippon Seiyaku) containing 20% of human serum albumin. To the resultant mixture was added 0.7 milliliter of a 1.5% (w/v) solution of sodium hyaluronate (average molecular weight: ca. 500,000 daltons) in physiological saline for injection (Fuso Pharmaceutical). A glass vial (capacity: ca. 5 milliliters) containing these solutions was hermetically stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 52

To 0.023 milliliter of a human granulocyte colony stimulating factor preparation (Nupogen; Amgen) containing, per milliliter, 300 micrograms of a recombinant human G-CSF, 50 milligrams of mannitol and 0.004% of Tween 80 was added 1.039 milliliters of physiological saline for injection, followed by further addition of 4 microliters of Albumin Nichiyaku (Nippon Seiyaku) containing 20% of human serum albumin. To the resultant mixture was added 1.039 milliliters of a 1% solution of sodium hyaluronate (average molecular weight: ca. 800,000–900,000 daltons; Artz Injection; Seikagaku Corporation, Japan). A glass vial (capacity: ca. 5 milliliters) containing these solutions was tightly stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 53

To 0.023 milliliter of a human granulocyte colony stimulating factor preparation (Nupogen; Amgen) containing, per milliliter, 300 micrograms of a recombinant human G-CSF, 50 milligrams of mannitol and 0.004% Tween 80 was added 1.377 milliliters of physiological saline for injection, followed by further addition of 4 microliters of Albumin Nichiyaku (Nippon Seiyaku) containing 20% of human serum albumin. To the resultant mixture was added 0.7 milliliter of a 1.2% (w/v) solution of sodium hyaluronate (average molecular weight: 1,800,000 daltons; Genzyme) in physiological saline for injection (Fuso Pharmaceutical). A glass vial (capacity: ca. 5 milliliters) containing these solutions was tightly stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 54

To 0.023 milliliter of a human granulocyte colony stimulating factor preparation (Nupogen; Amgen) containing, per milliliter, 300 micrograms of a recombinant human G-CSF, 50 milligrams of mannitol and 0.004% of Tween 80 was added 1.377 milliliters of physiological saline for injection, followed by further addition of 4 microliters of Albumin Nichiyaku (Nippon Seiyaku) containing 20% of human serum albumin. To the resultant mixture was added 0.7 milliliter of a 0.9% (w/v) solution of sodium hyaluronate (average molecular weight: ca. 2,300,000 daltons; Genzyme) in physiological saline for injection (Fuso Pharmaceutical). A glass vial (capacity: ca. 5 milliliters) containing these solutions was hermetically stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 55

In 1 milliliter of physiological saline for injection was dissolved 300 micrograms of an active human parathyroid hormone (PTH) fragment (Bachem Fine Chemicals, Switzerland) covering from the amino terminal to the 34th amino acid of PTH, followed by addition of 4 microliters of Albumin Nichiyaku (Nippon Seiyaku) containing 20% of human serum albumin. To the resultant mixture was added 1.5 milliliters of a 1.2% (w/v) solution of sodium hyaluronate (average molecular weight: ca. 1,800,000 daltons; Genzyme) in physiological saline (Fuso Pharmaceutical). A glass vial (capacity: ca. 10 milliliters) containing these solutions was subjected to rotary blending in a 200 milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 56

In 1 milliliter of physiological saline for injection was dissolved 300 micrograms of human parathyroid hormone (PTH) (Bachem Fine Chemicals), followed by addition of 4 microliters of Albumin Nichiyaku (Nippon Seiyaku) containing 20% of human serum albumin. To the resultant mixture was added 1.5 milliliters of a 1.2% (w/v) solution of sodium hyaluronate (average molecular weight: ca. 1,800, 000 daltons; Genzyme) in physiological saline for injection (Fuso Pharmaceutical). A glass vial (capacity: ca. 10 milliliters) containing these solutions was tightly closed and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 57

To a solution containing 100 ATU of hirudin (Peninsula Laboratories Inc., U.S.A.) is added physiological saline for injection to make the whole volume 1.4 milliliters. Then, 4 microliters of Albumin Nichiyaku (Nippon Seiyaku) containing 20% of human serum albumin is added. To the resultant mixture is added 0.7 milliliter of a 1.2% (w/v) solution of sodium hyaluronate (average molecular weight: ca. 1,800,000 daltons; Genzyme) in physiological saline (Fuso Pharmaceutical). A glass vial (capacity: ca. 5 milliliters) containing these solutions is tightly stoppered and subjected to rotary blending in a 200-milliliter eggplant-shaped flask equipped with a three-one motor (Heydon) by rotation (20–100 rpm) about its longitudinal axis for about one hour. The above procedure gives a long-acting dosing solution substantially free of bubbles.

EXAMPLE 58

In 1.4 milliliters of physiological saline was dissolved 10 milligrams of thyrotropic hormone releasing hormone (TRH; Bachem Fine Chemicals, Switzerland), followed by addition of 4 microliters of Albumin Nichiyaku (Nippon Seiyaku) containing 20% of human serum albumin. To the resultant mixture was added 0.7 milliliter of a 1.2% (w/v) solution of sodium hyaluronate (average molecular weight: ca. 1,800,000 daltons; Genzyme) in physiological saline for injection (Fuso Pharmaceutical). A glass vial (capacity: ca. 5 milliliters) containing these solutions was hermetically stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 59

In 1.4 milliliters of physiological saline was dissolved 10 milligrams of cefotiam dihydrochloride (Takeda Chemical Industries, Japan), followed by addition of 4 microliters of Albumin Nichiyaku (Nippon Seiyaku) containing 20% of human serum albumin. To the resultant mixture was added 0.7 milliliter of a 1.2% (w/v) solution of sodium hyaluronate (average molecular weight: ca. 1,800,000 daltons; Genzyme) in physiological saline for injection (Fuso Pharmaceutical). A glass vial (capacity: ca. 5 milliliters) containing these solutions was tightly stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

EXAMPLE 60

To each of two vials of Canferon-A300 (Takeda Chemical, Japan) containing 3 million international units (IU) of interferon alfa-2a and 5 mg of human serum albumin was added 1 ml of distilled water to provide an interferon alfa injection. 1.4 ml of the interferon alfa injection prepared as above (containing 4.2 million IU of interferon alfa-2a) and 0.7 ml of 1.5% (w/v) physiological saline solution of sodium hyaluronate (average molecular weight, 1,470,000 daltons) were put into a glass vial (capacity: ca. 5 ml). The glass vial containing these solutions was hermetically closed and subjected to rotary blending in a 200 ml egg-plant-type flask equipped with a three-one motor (Heydon, Japan) by rotation about its longitudinal axis (20–100 rpm) for about 1 hour. The procedure gave a long-acting dosing solution substantially free of bubbles.

EXAMPLE 61

To 0.4 milliliter of a solution of recombinant human basic FGF mutein CS23 (EP-281,822)(0.96 milligram protein/milliliter) were added 2.4 milliliters of physiological saline for injection and 15 microliters of Albumin Nichiyaku (Nihon Pharmaceutical, Japan), a 20% solution of human serum albumin, followed by addition of 1.4 milliliters of 1.5% (w/v) physiological saline solution of sodium hyaluronate (average molecular weight, 1470,000 daltons). A glass vial (capacity: ca. 12 ml) was hermetically closed and subjected to rotary blending in a 200 ml egg-plant type flask equipped with a three-one motor (Heydon, Japan) by rotation about its longitudinal axis (20–100 rpm) for about 1 hour. The procedure gave a long acting dosing solution substantially free of bubbles.

EXAMPLE 62

In 2 ml of physiological saline for injection (Fuso Pharmaceutical, Japan) was added 300 micrograms of parathyroid hormone (PTH) (Bachem Fine Chemicals). A glass vial (capacity: ca. 5 ml) filled with the above injection was added 4 microliters of Nichiyaku Albumin (Nihon Seiyaku) containing 20% (v/v) of human serum albumin and 1 ml of a 1.5% (w/v) solution of sodium hyaluronate (average molecular weight 1,470,000; Genzyme) in physiological saline. The glass vial containing these solutions was hermetically closed and subjected to rotary blending by rotation about its longitudinal axis (20–100 rpm) in a three-one motor (Heydon; Japan) for about one hour. The procedure gave a long-acting dosing solution substantially free of bubbles.

Experimental Example 11

The following two injections were further prepared and subjected to testing.

Comparative Preparation 20

To 0.35 milliliter of a solution of recombinant human basic FGF mutein CS23 (EP-281,822) (0.96 milligram protein/milliliter) was added 1.225 milliliters of physiological saline for injection.

Comparative Preparation 21

To 0.36 milliliter of a solution of recombinant human basic FGF mutein CS23 (EP-281,822) (0.96 milligram protein/milliliter) were added 1.26 milliliters of physiological saline for injection and 8.1 milligrams of sodium hyaluronate (average molecular weight 1,470,000 daltons; Genzyme).

The injection of Example 12 was subcutaneously administered to 8-week-old male SD rats on their back at a dose of 160 micrograms/kilogram. As controls, Comparative Preparation 20 and Comparative Preparation 21 were administered in the same manner. Before administration and at regular intervals after administration, about 0.4-milliliter portions of blood were collected. The serum was separated from each blood sample and assayed for serum rhbFGF mutein CS23 level by ELISA. The results obtained are shown in FIG. 11. The figure graphically shows the courses of change in blood mutein level after administration of Comparative Preparation 20(o), Comparative Preparation 21(□), and the rhbFGF mutein CS23 injection of Example 12 (•), respectively. Rats were used in groups of 5. In each graph, each dot indicates a mean value and each bar a standard error (S.E.).

It was found that while rhbFGF mutein CS23 rapidly disappeared from the blood in the group given Comparative Preparation 20 (simple rhbFGF mutein CS23 solution), the blood rhbFGF mutein CS23 level was maintained high in the group given Comparative Preparation 21 containing hyaluronic acid owing to the effect of hyaluronic acid. It was found, however, that the blood mutein level was maintained still higher at hour 1 and hour 4 after administration in the group given the injection of Example 12 prepared by adding hyaluronic acid and serum albumin to rhbFGF mutein CS23 as compared with the group given Comparative Preparation 21 prepared by adding hyaluronic acid alone.

Experimental Example 12

The following two injections were further prepared and subjected to testing.

Comparative Preparation 22

Three milligrams of pig insulin (26.8 units/milligram; Diosynth) was dissolved in 1.5 milliliters of 0.1N hydrochloric acid and then 1.65 milliliters of physiological saline for injection was added, followed by addition of 15.75 milligrams of sodium hyaluronate (average molecular weight 1,470,000 daltons; Genzyme).

Comparative Preparation 23

Physiological saline for injection 2 milliliters

The insulin injection of Example 47 and Comparative Preparation 22 were respectively administered subcutaneously to 8-week-old male SD rats on their back at a dose of 200 micrograms/rat. In a control group, Comparative Preparation 23, namely physiological saline for injection, was administered at the same voluminal dose as used in administering the preparation of Example 47 and Comparative Preparation 22. Before administration and at regular intervals after administration, about 0.5-milliliter portions of blood were collected and the serum samples derived therefrom were assayed for serum glucose level using a glucose C test kit (Wako Pure Chemical).

The results obtained are shown in FIG. 12. The figure shows the time courses of the serum glucose level as respectively revealed in the group given Comparative Preparation 23 (physiological saline) (o), the group given Comparative Preparation 22 (solution of pig insulin plus hyaluronic acid) (o colored black) and in the group given the solution of Example 47 containing pig insulin plus a combination of hyaluronic acid and serum albumin (Δ). Rats were used in groups of 5 and, in FIG. 12, each dot indicates a mean value. In the group given Comparative Preparation 23 (physiological saline), the serum glucose level remained almost unchanged. In the groups given Comparative Preparation 22 and the preparation Example 47, respectively, the serum glucose-level was suppressed to substantially the same extent until minute 240 postadministration. At minute 360 postadministration and thereafter, the serum glucose level reduction lasted for a longer period in the group given the preparation of Example 47. At minute 540 postadministration, the serum glucose level had substantially returned to a normal value range in the Comparative Preparation 22 group while, in the Example 47 group, the level was still about two thirds of that in the physiological saline (Comparative Preparation 23) group. This indicates that while the combination of insulin and hyaluronic acid is said to prolong the effect of the peptide, further addition of serum albumin to this system can cause the pharmacological effect to last still longer at the same dose of insulin and in the same amount of hyaluronic acid.

Experimental Example 13

The following injections were further prepared and tested.

Comparative Preparation 24

To 0.0233 milliliter of a human granulocyte colony stimulating factor preparation (Nupogen; Amgen) containing, per milliliter, 300 micrograms of a recombinant human G-CSF, 50 milligrams of mannitol and 0.004% of Tween 80 was added 1.377 milliliters of physiological saline for injection. To the resultant mixture was added 0.7 milliliter of a 1.5% (w/v) solution of sodium hyaluronate (average molecular weight: 1,470,000 daltons; Genzyme) in physiological saline (Fuso Pharmaceutical). A glass vial (capacity: ca. 5 milliliters) containing these solutions was hermetically stoppered and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

Comparative Preparation 25

To 0.0233 milliliter of a human granulocyte colony stimulating factor preparation (Nupogen; Amgen) containing, per milliliter, 300 micrograms of a recombinant human G-CSF, 50 milligrams of mannitol and 0.004% of Tween 80 was added 2.077 milliliters of physiological saline for injection.

Comparative Preparation 26

To 1.4 milliliters of physiological saline for injection was added 0.7 milliliter of a 1.5% (w/v) solution of sodium hyaluronate (average molecular weight: 1,470,000 daltons; Genzyme) in physiological saline for injection (Fuso Pharmaceutical). A glass vial (capacity: ca. 5 milliliters) containing these solutions was hermetically closed and subjected to rotary blending in a 200-milliliter eggplant-shaped flask equipped with a three-one motor (Heydon) by rotation (20–100 rpm) about its longitudinal axis for about one hour. The above procedure gave a long-acting dosing solution substantially free of bubbles.

Eight-week-old male SD rats were subcutaneously dosed by injection at their back, with the human G-CSF-containing preparation of Example 50, Comparative Preparation 24 or Comparative Preparation 25 in a volume of 0.3 milliliter. In a control group, the solution of sodium hyaluronate in physiological saline for injection (Comparative Preparation 26) was administered in a volume of 0.3 milliliter. Before administration and serially after administration, about 0.1 milliliter of blood was withdrawn (EDTA•2 Na used as anticoagulant). Peripheral leukocytes, erythrocytes and platelets were counted using a CC-180A microcell counter (Toa Iyo Denshi, Japan). Peripheral neutrophil, lymphocyte, monocyte and eosinophil counts were estimated by multiplying the respective cell occurrence frequencies, as found by typing, under a microscope, of 200 leukocytes for each Giemsa-stained smear preparation, by the leukocyte count.

The results thus obtained are shown in FIG. 13. In the control group (o) given the aqueous hyaluronic acid solution (Comparative Preparation 26), the peripheral blood neutrophil count changed little. In the positive control group (o colored black) given the human G-CSF solution (Comparative Preparation 25), the peripheral blood 16 hours after administration showed a nearly doubled neutrophil count as compared with the control group. In the group (Δ) given Comparative Preparation 24, which contained hyaluronic acid additionally, the peripheral blood showed a further increase in neutrophil count. In the group (□) given the preparation of Example 50, which contained human G-CSF in combination with hyaluronic acid plus human serum albumin, the peripheral blood showed a still further increase in neutrophil count as compared with the group given Comparative Preparation 24. At 24 hours after administration, the peripheral blood neutrophil counts in the groups given Comparative Preparation 24 and Comparative Preparation 25, respectively, were already at substantially the same level as in the control group whereas, in the group given the preparation of Example 50, the neutrophil count was still approximately twice the level in the control group. These results indicate that the addition of human serum albumin can further potentiate the pharmacological effect prolonging action of hyaluronic acid. In the figure, each point indicates a mean of 5 rats.

Experimental Example 14

The following injection was further prepared and tested.

Comparative Preparation 27

To each of two vials of Canferon-A300 (Takeda Chemical, Japan) containing 3 million international units (IU) of interferon alfa-2a and 5 mg of human serum albumin was added 1 ml of distilled water to provide an interferon alfa injection. 1.4 ml of the interferon alfa injection prepared as above (containing 4.2 million IU of interferon alfa-2a) and 0.7 ml of physiological saline for injection were put into a glass vial (capacity: ca. 5 ml) and mixed gently.

Eight-week-old male SD rats were subcutaneously dosed by injection at their back, with the interferon alfa-2a-containing preparation of Example 60 or Comparative Preparation 27 in volume of 0.3 milliliter. Before administration and serially after administration, about 0.4 ml portions of blood were collected. The serum was separated from each blood sample and assayed for serum interferon alfa 2-a level by ELISA.

The results are plotted in FIG. 14. Interferon alfa 2-a was rapidly absorbed from the injection site in the control group treated with Comparative Preparation 27 and the serum interferon alfa 2-a concentration fell with time (o). On the other hand, in the group treated with the preparation of Example 60 containing hyaluronic acid, human serum albumin, and interferon alfa 2-a, the serum interferon alfa 2-a concentrations were higher compared with those of the control group from 1 hour till 8 hours after administration (•). These results manifest the positive effect of the combination of hyaluronic acid, human serum albumin, and interferon alfa 2-a in sustaining the serum drug concentrations. Each point represents the mean of five rats.

Experimental Example 15

The following composition was further prepared and tested.

Comparative Preparation 28

To 0.4 milliliter of a solution of recombinant human basic FGF mutein CS23(EP-281,822) (0.96 milligram protein/milliliter) was added 3.6 milliliters of physiological saline for injection.

Eight-week-old male SD rats fasted for 24 hours were lightly anesthetized by intraperitoneal injection of sodium pentobarbital (Somnopentyl, Pitman Moore, U.S.A.) and were orally administered 1 milliliter of either the preparation of Example 61 or the preparation of Comparative Preparation 28 to stomach. At 30 minutes post administration, incision was made at abdomen and the content of the stomach was collected. Portion of the collected content was immediately centrifuged (Microfuge B, Beckman, U.S.A.), and a 50 microliters aliquot of the supernatant was mixed with a 100 microliters aliquot of a protease inhibitor (Aprotinin, Sigma, U.S.A.) and stored at −40° C. for further determination of CS23 concentration by enzyme immno assay.

| | CS23 Concentration (pg/ml) |
|---|---|
| Comparative Preparation 28 | 1768 |
| Preparation of Example 61 | 8448 |

The results manifest the positive effect of the combination of hyaluronic acid, human serum albumin, and recombinant human basic FGF mutein, CS23, in persisting in succus gastricus inside stomach.

Experimental Example 16

The following composition was further prepared and tested.

Comparative Preparation 29

In 2 ml of physiological saline for injection (Fuso Pharmaceutical) was added 300 micrograms of parathyroid hormone (Bachem Fine Chemicals).

The composition of Example 62 (•) and Comparative Preparation 29 (o) were respectively administered subcutaneously at the back of 8-week-old male SD rats in a volume of 0.2 ml. Before administration and serially after administration, about 0.4 ml of blood was withdrawn and serum sample was separated for the determination of PTH by radio immunoassay. As shown in FIG. 15, at 2 hours and 3 hours post administration the serum PTH level was significantly higher in the group of given Example 62 than in the group given Comparative Preparation 29.

The results manifest the positive effect of the combination of hyaluronic acid, human serum albumin, and PTH in prolonging the serum level of PTH.

The following references, which are referred to for their disclosures at various points in this application, are incorporated herein by reference.

Japanese Patent Application Laid-open No. 62-129226 (1987)
European Patent Publication No. 224,987
Japanese Patent Application Laid-open No. i-287041 (1989)
Japanese Patent Application Laid-open No. 2-213 (1990)
Japanese Patent Application Laid-open No. 3-4790 (1991)
J. Biol. Chem., 252, 5558–5564 (1977)
J. Biol. Chem., 262, 17156–17161 (1987)
Nature, 313, 806–810 (1985)
Proc. Natl. Acad. Sci. U.S.A., 82, 7580–7585 (1985)
J. Biol. Chem., 262, 17156–17161 (1987)
Proc. Natl. Acad. Sci. U.S.A., 86, 7819–7822 (1989)
Endocrinology, 116, 2293–2299 (1985)
Biochem. Biophys. Acta P, 1038, 125–129 (1990)
Agri. Biol. Chem., 52, 1575–1581 (1988)
Endocrinology, 129, 324 (1991)
The EMBO Journal, 11, 1867 (1992)
Japanese Patent Application Laid-open No. 121273/1975
U.S. Pat. No. 3,959,247
Japanese Patent Application Laid-open No. 116465/1977
U.S. Pat. No. 4,100,152
EP-281,822
Japanese Patent Application Laid-open No. 115528/1986
EP-145,390
Japanese Patent Application Laid-open No. 78799/1986
EP-176,299
Japanese Patent Application Laid-open No. 29285/1982
EP-45,222
Japanese Patent Application Laid-open No. 16685/1983
EP-70,656.

What we claim is:

1. A water-soluble composition which comprises (a) a pharmacologically active polypeptide secreted by an animal body or its derivative or a chemically synthesized pharmacologically active substance, (b) a water-soluble species of hyaluronic acid or its non-toxi salt and (c) a water-soluble protein injectable into body fluids without showing any substantial pharmacological activity.

2. A water-soluble composition as claimed in claim 1, wherein the pharmacologically active polypeptide is cytokines, peptide hormones, growth factors, the factors that affect cardiovasculr system, the factors that affect central and peripheral nerve system, the factors that affect body fluid electrolytes and blood organic constituents, the factors that affect bone and skeletal system, the factors that affect gastrointestinal system, the factors that affect immune system, the factors that affect respiratory system, the factors that affect genital system or enzymes, or its mutein, derivative, analog, homolog, or active fragment.

3. A water-soluble composition as claimed in claim 1, wherein the pharmacologically active polypeptide is interferons, interleukins, erythropoietin, granulocyte colony stimulating factor (G-CSF), granylocyte-macrophage colony stimulating factor (GM-CSF), macrophage colony stimulating factor (M-CSF), fibroblast growth factor (FGF), tumor necrotizing factor (TNF), parathyroid hormone (PTH), calcitonin, insulin or leutenizing hormone-releasing hormone (LH-RH).

4. A water-soluble composition as claimed in claim 1, wherein the chemically synthesized pharmacologically active substance is those that affect cardiovascular system, those that affect cell attachment, those that affect central and peripheral nerve system, those that affect body fluid electrolytes and blood organic constituents, those that affect bone and skeletal system, those that affect gastrointestinal system, those that affect immune system or those that affect infective microorganisms.

5. A water-soluble composition as claimed in claim 1, wherein the water-soluble protein is human serum albumin.

6. A water-soluble composition as claimed in claim 1, which shows a viscosity of not more than 500 cp in an aqueous solution form.

7. A water-soluble composition as claimed in claim 1, which contains the water-soluble hyaluronic acid in an amount of about 0.01 to 3% (weight to volume).

8. A water-soluble composition as claimed in claim 1, which contains about 0.001 to 5% (weight to volume) of serum albumin as the water-soluble protein.

9. A water-soluble composition as claimed in claim 1, which contains about 0.001 to 5% (weight to volume) of a globulin as the water-soluble protein.

10. A water-soluble composition as claimed in claim 1, which contains about 0.001 to 1% (weight to volume) of collagen as the water-soluble protein.

11. A water-soluble composition as claimed in claim 1, which contains about 0.001 to 1% (weight to volume) of gelatin as the water-soluble protein.

12. A water-soluble composition as claimed in claim 1, which is in the form of preparation for parenteral administration.

13. A water-soluble composition as claimed in claim 12, which is in the form of an injectable preparation.

14. A water-soluble composition as claimed in claim 1, wherein the weight ratio of the pharmacologically active substance to hyaluronic acid or its nontoxic salt is in the range of about 0.0001:1 to about 10:1, and the weight ratio of water-soluble protein to hyaluronic acid or its nontoxic salt is in the range of about 0.001:1 to about 100:1.

* * * * *